US009518016B2

(12) United States Patent
Madiraju et al.

(10) Patent No.: US 9,518,016 B2
(45) Date of Patent: Dec. 13, 2016

(54) INSULIN SECRETION PROMOTING AGENTS

(71) Applicant: VAL-CHUM, LIMITED PARTNERSHIP, Montreal (CA)

(72) Inventors: Murthy Madiraju, Brossard (CA); Marc Prentki, Mont-Royal (CA); Erik Joly, Blainville (CA)

(73) Assignee: VAL-CHUM, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 15/160,362

(22) Filed: May 20, 2016

(65) Prior Publication Data

US 2016/0264527 A1    Sep. 15, 2016

Related U.S. Application Data

(62) Division of application No. 14/236,852, filed as application No. PCT/CA2012/000721 on Jul. 31, 2012, now Pat. No. 9,371,285.

(60) Provisional application No. 61/514,563, filed on Aug. 3, 2011.

(51) Int. Cl.
   *C07D 213/40* (2006.01)
   *C07C 271/44* (2006.01)

(52) U.S. Cl.
   CPC ........... *C07D 213/40* (2013.01); *C07C 271/44* (2013.01)

(58) Field of Classification Search
   None
   See application file for complete search history.

(56) References Cited

FOREIGN PATENT DOCUMENTS

WO    WO 2011/140659    11/2011

OTHER PUBLICATIONS

Li et al., 129(31) J. Am. Chem. Soc. 9594-9595 (2007).*
Bachovchin, et al., PNAS USA. 107(49):20941-6, 2010.
Hohmeir et al. Diabetes. 49:424-430, 2000.
International Preliminary Report on Patentability in International Application No. PCT/CA2012/000721 mailed Feb. 4, 2014.
Peyot et al., J Biol Chem. 284:16848-16859, 2009.
Roduit et al. Diabetes. 53:1007-1019, 2004.
Search Report and Written Opinion in International Application No. PCT/CA2012/000721 mailed Nov. 5, 2012.
Akiba, Y. et al.. "Transient Receptor Potential Vanilloid Subfamily 1 Expressed in Pancreatic Islet Beta Cells Modulates Insulin Secretion in Rats". Biochem Biophys Res Commun 321: 219-225. 2004.
Alevizos, A. et al. "Insulin Secretion and Capsaicin". Am J. Clin Nutr 85: 1165-1166.2007.
Ashiya M. et al. "Non-Insulin Therapies for Type 2 Diabetes". Nature Reviews Drug Discovery 6:777-778. 2007.
Barbasa, M. et al. "Calcium Signals in Rat Pancreatic INS-1 Beta Cells". Ethnicity and Disease 18: S1-62-S61-64, 2008.
Bermudez-Silva, F.J. et al. "Presence of functional cannabinoid receptors in human endocrine pancreas.". Diabetologia. vol. 51. pp. 476-487. 2008.
Bisogno, T. et al. "Cloning of the First snl-DAG Lipases Points to the Spatial and Temporal Regulation of Endocannabinoid Signaling in the Brain". J. Cell Biol. 163: 463-468. 2003.
Blankman, J.L. et al. "A Comprehensive Profile of Brain Enzymes that Hydrolyze the Endocannabinoid 2-Arachidonoylglycerol". Chem Biol. vol. 14. No. 12. pp. 1347-1356. 2007.
Bluher, M. et al. "Dysregulation of the Peripheral and Adipose Tissue Endocannabinoid System in Human Abdominal Obesity". Diabetes. 55: 3053-3060. 2006.
Brindley, D.N. et al. "Lipid Phosphate Phosphatases and Signaling". J. Lipid Res 50 Suppl.: S225-230, 2009.
Delghingaro-Augusto, V. et al. "Islet Beta Cell Failure in the 60% Pancreatectomised Obese Hyperlipidaemic Zucker Fatty Rat: Severe Dysfunction with Altered Glycerolipid Metabolism without Steatosis or a Falling Beta Cell Mass". Diabetologia. Vo. 52. pp. 1122-1132. 2009.
Di Marzo, V. et al. "Leptin-regulated Endocannabinoids are Involved in Maintaining Food Intake". Nature. 410: 822-825. 2001.
Di Marzo, V. et al. "The Endocannabinoid System and its Therapeutic Exploitation". Nat. Rev. Drug Discov. 3: 771-784. 2004.
Engeli, S. et al. Activation of the Peripheral Endocannabinoid System in Human Obesity. Diabetes. 54: 2838-2843. 2005.
Gavva, N. R. et al. "AMG 9810 [(E)-3-(4-t-butylphenyl)-N-(2,3-dihydrobenzo[b][1,4] dioxin-6-yl)acrylamide], a Novel Vanilloid Receptor 1 (TRPV1) Antagonist with Antihyperalgesic Properties". J Pharmacol Exp Ther 313: 474-484. 2005.
Gotoh, M. et al. "Reproducible High Yield of rat Islets by Stationary in vitro Digestion Following Pancreatic Ductal or Portal Venous Collagenase Injection". Transplantation. vol. 43, No. 5. pp. 725-730. 1987.
Gram, D.X. et al. "Sensory Nerve Desensitization by Resiniferatoxin Improves Glucose Tolerance and Increases Insulin Secretion in Zucker Diabetic Fatty Rats and is Associated with Reduced Plasma Activity of Dipeptidyl Peptidase IV". Eur J Pharmacol 509: 211-217. 2005.
Gram, D.X. et al. "Capsaicin-Sensitive Sensory Fibers in the Islets of Langerhans Contribute to Defective Insulin Secretion in Zucker Diabetic Rat, an Animal Model for Some Aspects of Human Type 2 Diabetes". Eur J. Neurosci. 25: 213-223. 2007.
Hohmeir, H.E, et al. "Isolation of INS-1-Derived Cell Lines With Robust ATPSensitive K+ Channel-Dependent and -Independent Glucose-Stimulated Insulin Secretion". Diabetes. vol. 49. pp. 424-430. Mar. 2000.
Hoover, H.S. et al. "Selectivity of Inhibitors of Endocannabinoid Biosynthesis Evaluated by Activity-Based Protein Profiling". Bioorg Med Chem Lett. 18: 5838-5841. 2008.

(Continued)

Primary Examiner — Timothy R Rozof
(74) Attorney, Agent, or Firm — Norton Rose Fulbright US LLP

(57) ABSTRACT

The present disclosure relates to novel compounds, compositions containing same and methods for treating or preventing a condition associated with a deficient insulin secretion such as diabetes and metabolic syndrome in a subject in need thereof.

14 Claims, 1 Drawing Sheet

(56) References Cited

OTHER PUBLICATIONS

Iwasaki, Y. et al. "Monoacylglycerols Activate Capsaicin Receptor, TRPV1." *Lipids* 43: 471-483. 2008.
Jahanshahi, P. et al. "Evidence of Diminished Glucose Stimulation and Endoplasmic Reticulum Function in Nonoscillatory Pancreatic Islets". *Endocrinology*. vol. 150(2). pp. 607-615. Feb. 2009.
Jing, X. et al. "CaV2.3 Calcium Channels Control Second-Phase Insulin Release". *J. Clin Invest* 115: 146-154. 2005.
Juan-Pico, P. et al. "Cannabinoid Receptors Regulate Ca(2+) Signals and Insulin Secretion in Pancreatic Beta-Cell". *Cell Calcium* 39: 155-162. 2006.
Konrad, R.J. et al. "Diacylglycerol Hydrolysis to Arachidonic Acid is Necessary for Insulin Secretion from Isolated Pancreatic Islets: Sequential Actions of Diacylglycerol and Monoacylglycerol Lipases". *Biochemistry* 33: 13284-13294. 1994.
Kwan, EP, et al. "Munc13-1 Deficiency Reduces Insulin Secretion and Causes Abnormal Glucose Tolerance". *Diabetes* 55: 1421-1429. 2006.
Long, J.Z. et al. "Characterization of Monoacylglycerol Lipase Inhibition Reveals Differences in Central and Peripheral Endocannabinoid Metabolism". *Chem Biol.* 16: 744-753, 2009.
Masiello, P. et al. "The Antilipolytic Agent 3,5-dimethylpyrazole Inhibits Insulin Release in Response to Both Nutrient Secretagogues and Cyclic Adenosine Monophosphate Agonists in Isolated Rat Islets". *Metablolism* 51: 110-114. 2002.
Matias, I. et al. "Regulation, Function and Dysregulation of Endocannabinoids in Models of Adipose and Beta-Pancreatic Cells and in Obesity and Hyperglycemia". *J. Clin. Endocrinol. Metab.* 91:3171-3180. 2006.
Max, D. et al. "High Expression of the Evolutionarily Conserved Alpha/Beta Hydrolase Domain Containing 6 (ABHD6) in Ewing Tumors". *Cancer Sci.* 100: 2383-2389. 2009.
Mehta et al. *Journal of Chromatography* B, 719 pp. 9-23. 1998.
Moesgaard, S.G. et al. "Sensory Nerve Inactivation by Resiniferatoxin Improves Insulin Sensitivity in Male Obese Zucker Rats". *Am J. Physiol Endocrinol Metab* 288: E 1137-1145. 2005.
Motter, A.L. et al. "TRPV1-Null Mice are Protected from Diet-Induced Obesity". *FEBS Lett* 582: 2257-2262. 2008.
Mulder, H. et al. "Inhibition of Lipase Activity and Lipolysis in Rat Islets Reduces Insulin Secretion". *Diabetes* 53: 122-128. 2004.
Nathan, DM, et al. "Medical Management of Hyperglycaemia in Type 2 Diabetes Mellitus: A Consensus Algorithm for the Initiation and Adjustment of Therapy: A Consensus Statement from the American Diabetes Association and the European Association for the Study of Diabetes". *Diabetologia* 52:17-30, 2009.
Nolan, C.J. et al. "Beta Cell Compensation for Insulin Resistance in Zucker Fatty Rats : Increased Lipolysis and Fatty Acid Signalling". *Diabetologia* 49: 2120-2130. 2006.
Nolan, C.J. et al., "Fatty Acid Signaling in the {beta}-Cell and Insulin Secretion" *Diabetes* 55 Suppl 2: S16-23, 2006.
Nolan, C.J. et al. "The Islet Beta-Cell: Fuel Responsive and Vulnerable". *Trends Endocrinol Metab* 19: 285-291. 2008.

Pagotto, U. et al. "The Emerging Role of the Endocannabinoid System in Endocrine Regulation and Energy Balance". *Endocr Rev.* 27:73-100. 2006.
Pedersen, M.G. et al. "Newcomer Insulin Secretory Granules as a Highly Calcium-Sensitive Pool". *Proc Natl Acad Sci USA* 106: 7432-7436. 2009.
Peyot, M.L. et al. "Hormone-Sensitive Lipase has a Role in Lipid Signaling for Insulin Secretion but is Nonessential for the Incretin Action of Glucagon-Like Peptide 1". *Diabetes*. vol. 53. pp. 1733-1742. 2004.
Peyot, M.L. et al. "Adipose Tridlyceride Lipase is Implicated in Fuel- and Non-Fuel-Stimulated Insulin Secretion". J. Biol. Chem. vol. 284. pp. 16848-16859. 2009.
Prentki, M. et al. "Ca2+, cAMP, and Phspholipid-Derived Messengers in Coupling Mechanisms of Insulin Secretion". *Physiol Rev* 67:1185-1248. 1987.
Prentki, M. et al. "Glycerolipid Metabolism and Signaling in Health and Disease". *Endocr Rev* 29: 647-676. 2008.
Prentki, M. et al. "Islet beta cell failure in type 2 diabetes". *J Clin Invest* 116:1802-1812. 2006.
Razavi, R. et al. "TRPV1+ Sensory Neurons Control Beta Cell Stress and Islet Inflammation in Autoimmune Diabetes". *Cell* 127: 1123-1135. 2006.
Rhee, J.S. et al. "Beta Phorbol Ester- and Diacylglycerol-Induced Augmentation of Transmitter Release is Mediated by Munc13s and not by PKCs". *Cell.* 108: 121-133. 2002.
Rodriguez de Fonseca, F. et al. "The Endocannabinoid System: Physiology and Pharmacology". *Alcohol Alcohol.* 40:2-14, 2005.
Roduit, R. et al. "A Role for Hormone-Sensitive Lipase in Glucose-Stimulated Insulin Secretion: A Study in Hormone-Sensitive Lipase-Deficient Mice". *Diabetes* 50: 1970-1975. 2001.
Sheu, L. et al. "Regulation of Insulin Exocytosis by Munc13-1". *J. Biol. Chem.* 278: 27556-27563. 2003.
Suri, A. et al. "The Emerging Role of TRPV1 in Diabetes and Obesity". *Trends Pharmacol Sci.* 29:29-36. 2008.
Venkatachalam, K. et al. "TRP Channels". Annu Rev Biochem. 76: 387-417. 2007.
Vriens, J. et al. "Pharmacology of Vanilloid Transient Receptor Potential Cation Channels". *Mol. Pharmacol.* 75: 1262-1279. 2009.
Weiwei, L. et al. "A Functional Proteomic Strategy to Discover Inhibitors for Uncharacterized Hydrolases". J. Am Chem Soc. vol. 129:9594-9595. 2007.
Extended European Search Report issued in EP 12819370.3, mailed Nov. 18, 2014.
Bachovchin et al., "Supplementary Material for Superfamily-wide portrait of serine hydrolase inhibition achieved by library-versus-library screening", *Proceedings of the National Academy of Sciences* 107:49, 2010.
Dhillon, "Sitagliptin—A Review of its Use in the Management of Type 2 Diabetes Mellitus", *Drugs* 70(4):489-512, 2010.
Li et al., "A Functional Proteomic Strategy to Discover Inhibitors for Uncharacterized Hydrolases", *J. Am. Chem. Soc.* 129(31):9594-9595, 2007.

* cited by examiner

INSULIN SECRETION PROMOTING AGENTS

CROSS-REFERENCE TO RELATED APPLICATIONS

This application is a divisional of U.S. patent application Ser. No. 14/236,852 filed 7 Feb. 2014, which is a national phase application under 35 U.S.C. §371 of International Application No. PCT/CA2012/000721 filed 31 Jul. 2012, which claims priority to U.S. Provisional Application No. 61/514,563 filed 3 Aug. 2011. The entire contents of each of the above-referenced disclosures is specifically incorporated herein by reference without disclaimer.

FIELD OF THE DISCLOSURE

The present disclosure relates to novel compounds, compositions containing same and methods for treating or preventing a condition associated with a deficient insulin secretion such as diabetes and metabolic syndrome in a subject in need thereof.

BACKGROUND OF THE DISCLOSURE

Therapeutic management of conditions associated with deficient insulin secretion has been globally identified as a challenge. For example, management of type-2 diabetes (T2D) currently is achieved by drugs that either reduce insulin resistance, reduce liver gluconeogenesis or elevate insulin secretion by β-cells in order to control blood glucose levels. Remarkable progress has been made in the last decade in deducing the mechanisms of fuel-stimulated insulin secretion (IS) in the pancreatic β-cell and while the role of enhanced $Ca^{2+}$ influx in the triggering of $K_{ATP}$-dependent pathway of glucose stimulated insulin secretion (GSIS) is established, the signaling molecules implicated in the amplification of $K_{ATP}$-independent pathway(s) remain to be defined. Much support has been provided for the concept that lipid mediators and glycerolipid/free fatty acid (GL/FFA) cycling, which is glucose-responsive in the β-cell, play key role in GSIS. GL/FFA cycling refers to the cyclic process of FFA esterification with glycerol to synthesize GL, followed by its hydrolysis releasing the FFA that can be re-esterified.

GL/FFA cycling is active in many cells allowing for continuous production of neutral (mono-, di- & tri-acylglycerols (MAG; DAG; TG)) and complex lipids and phospholipids (PL). Various intermediates of GL/FFA cycling including FFA, fatty acyl-CoAs (FACoA), DAG, etc., likely regulate GSIS, though the mechanisms by which they influence this process remain uncertain. The significance of GL/FFA cycling for insulin secretion became evident from studies showing curtailed GSIS in rat islets upon lipolysis inhibition by the pan-lipase inhibitors 3,5-dimethylpyrazole and orlistat, and also by the deletion of hormone-sensitive lipase (HSL) and adipose triglyceride lipase (ATGL). In the normoglycemic insulin resistant Zucker fatty rat, enhanced glucose-responsive GL/FFA cycling has been proposed to contribute to the hyperinsulinemia associated with sustained β-cell compensation of this animal. Defective pancreatic islet GL/FFA cycling at elevated glucose concentrations has been observed in various rodent models of type 2 diabetes. GL/FFA cycling intermediate, DAG, is thought to activate Munc-13-1, a vesicle priming protein, and also C-kinase enzymes, which play an important role in the exocytosis of insulin granules in β-cell. GL/FFA cycling and lipolysis derived monoacylglycerols (MAG) act as regulators of insulin secretion.

As discussed in Madiraju, M. et al in PCT/CA2011/050295, agents capable of augmenting monoacylglyceride (MAG) level at the inner surface of the cytoplasmic membrane of a cell or a cellular membrane derived therefrom including but not limited to membranes of mitochondria, nucleus, endoplasmic reticulum, etc and/or inhibiting the activity of the MAG-hydrolyzing α/β-Hydrolase Domain 6 (ABHD6) may be useful for increasing insulin secretion and as such for treating or preventing a condition associated with an insufficient insulin secretion, like diabetes.

SUMMARY

In an aspect of the disclosure, there is provided a compound of formula I

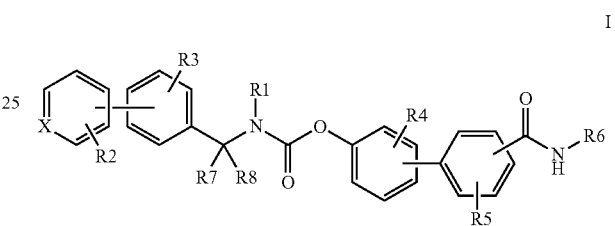

or a pharmaceutically acceptable salt or solvate thereof, wherein

X is N or CH;

R1 is lower linear or branched alkyl, cycloalkyl, lower linear or branched alkenyl, cycloalkenyl or aryl;

each of R2, R3, R4 and R5 is H or one or more independently selected substituent;

R6 is H, lower linear or branched alkyl, or cycloalkyl;

each of R7 and R8 is independently selected from H, lower alkyl or fluoride;

provided that said compound is other than compounds i), ii) iii) and iv):

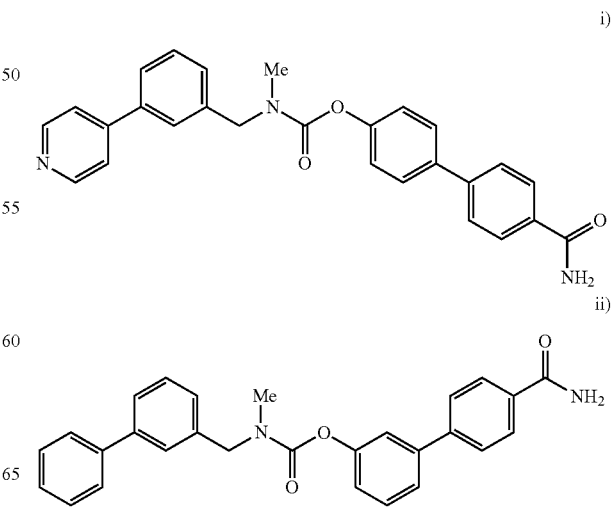

-continued

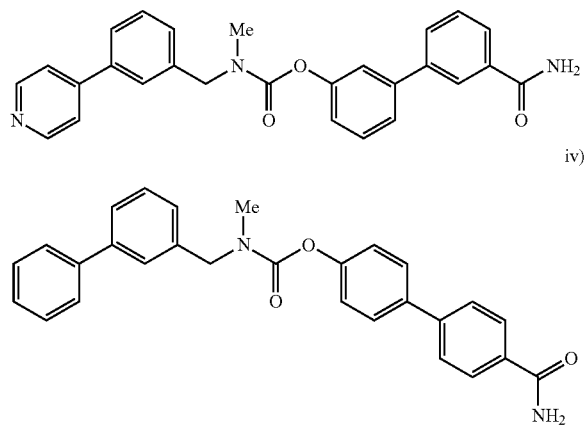

iii)

iv)

In another aspect of the disclosure, there is provided a pharmaceutical composition comprising a compound as defined herein or a pharmaceutically acceptable salt or solvate thereof, and an acceptable excipient.

In another aspect of the disclosure, there is provided a method for inhibiting ABHD6 in a subject in need thereof, comprising administering to the subject a therapeutically effective amount of a compound as defined herein or a pharmaceutically acceptable salt or solvate thereof, to a subject.

In yet another aspect of the disclosure, there is provided a method for treating or preventing a condition associated with a deficient insulin secretion in a subject in need thereof, comprising administering to the subject a therapeutically effective amount of a compound as defined herein, or a pharmaceutically acceptable salt or solvate thereof.

In another aspect of the disclosure, there is provided a method for increasing insulin secretion in a subject in need thereof comprising administering to the subject a therapeutically effective amount of a compound as defined herein or a pharmaceutically acceptable salt or solvate thereof.

Another aspect of the disclosure is to provide a method for the prevention or treatment of diabetes in a subject in need thereof comprising administering to the subject a therapeutically effective amount of a compound as defined herein or a pharmaceutically acceptable salt or solvate thereof.

In another aspect of the disclosure, there is provided a method for treating or preventing a condition associated with diabetes in a subject in need thereof comprising administering to the subject a therapeutically effective amount of a compound as defined herein or a pharmaceutically acceptable salt or solvate thereof.

Another aspect of the disclosure is to provide a method for the prevention or treatment of metabolic syndrome in a subject in need thereof comprising administering to the subject a therapeutically effective amount of a compound as defined herein or a pharmaceutically acceptable salt or solvate thereof.

In another aspect of the disclosure, there is provided a method for increasing a level of monoacylglyceride (MAG) in a cell of a subject, preferably in pancreatic β-cells, comprising administering to the subject a therapeutically effective amount of a compound as defined herein or a pharmaceutically acceptable salt or solvate thereof.

In another aspect of the disclosure, there is provided the use of a compound as defined herein or a pharmaceutically acceptable salt or solvate thereof, in the manufacture of a medicament for the treatment or prevention of a disease or condition described above or herein or for inhibiting ABHD6 or increasing insulin secretion or increasing a level of monoacylglyceride (MAG) in a cell of a subject, preferably in pancreatic β-cells.

In another aspect of the disclosure, there is provided the use of a compound as defined herein or a pharmaceutically acceptable salt or solvate thereof, for use in the treatment or prevention of a disease or condition described above or herein or for inhibiting ABHD6 or increasing insulin secretion or increasing a level of monoacylglyceride (MAG) in a cell of a subject, preferably in pancreatic β-cells.

In another aspect of the disclosure, there is provided the pharmaceutical composition as defined herein or use in the treatment or prevention of a disease or condition described above or herein or for inhibiting ABHD6 or increasing insulin secretion or increasing a level of monoacylglyceride (MAG) in a cell of a subject, preferably in pancreatic β-cells.

In one aspect, there is provided a process for preparing a compound of formula I as defined herein.

DESCRIPTION OF THE EMBODIMENTS

Figure 1:
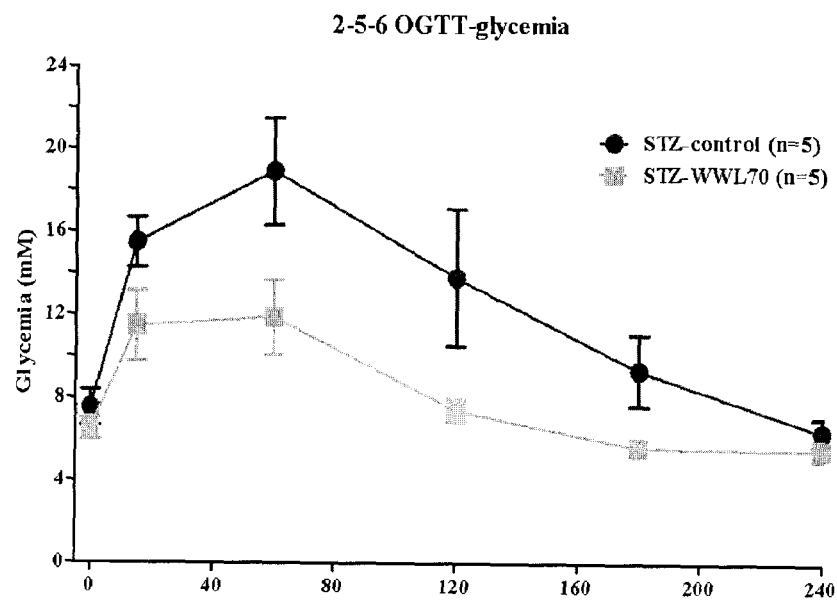
FIGS. 1 and 2 represent oral glucose tolerance test on mice.

In accordance with one embodiment, there is provided a compound described herein wherein the compound has the formula II

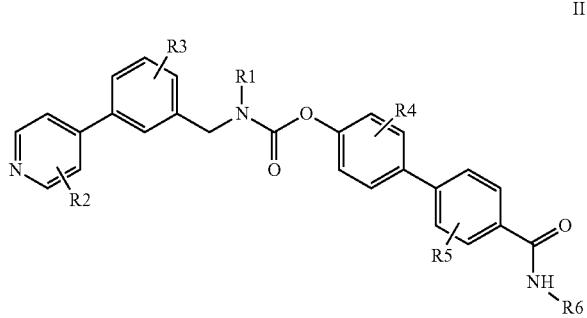

II or a pharmaceutically acceptable salt or solvate thereof, wherein X, R1, R2, R3, R4, R5 and R6 are as defined herein and provided that said compound is other than compounds i) and iv).

In accordance with one embodiment, the disclosure provides a compound of formula III:

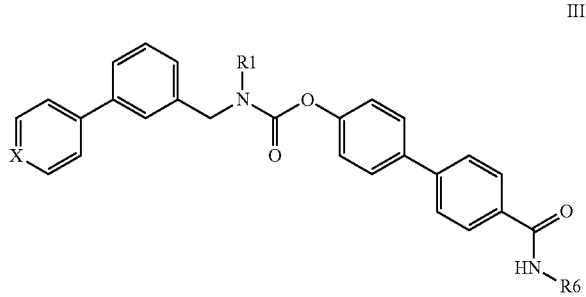

III wherein X, R1, and R6 are as defined herein and provided that said compound is other than compounds i) and iv).

In one embodiment, in compound of formula I and II, R2, R3, R4 and R5 are H.

In one embodiment, in compound of formula I and II, R2, R3, R4 and R5 are H or an independently selected substituent as defined herein.

In one embodiment, in compound of formula I, each of R7 and R8 is independently selected from H, C1-3 alkyl or fluoride.

In one embodiment, in compound of formula I, each of R7 and R8 is independently selected from H or C1-3 alkyl.

In one embodiment, in compound of formula I, each of R7 and R8 is independently selected from H, methyl, ethyl, n-propyl, i-propyl or cyclopropyl.

In one embodiment, in compound of formula I, each of R7 and R8 is H.

In one embodiment, in compound of formula I, II or III or a pharmaceutically acceptable salt or solvate thereof, X is CH.

In one embodiment, in compound of formula I, II or III or a pharmaceutically acceptable salt or solvate thereof, X is N.

In one embodiment, in compound of formula I, II or III or a pharmaceutically acceptable salt or solvate thereof, R1 is C1-6 linear or C3-6 branched alkyl, C3-6 cycloalkyl, C2-6 linear or branched alkenyl or aryl.

In one embodiment, in compound of formula I, II or III or a pharmaceutically acceptable salt or solvate thereof, R1 is C1-6 linear or C3-6 branched alkyl, C3-6 cycloalkyl, or optionally substituted phenyl.

In one embodiment, in compound of formula I, II or III or a pharmaceutically acceptable salt or solvate thereof, R1 is C1-3 linear alkyl, C3 branched alkyl, C3 cycloalkyl, or optionally substituted phenyl.

In one embodiment, in compound of formula I, II or III or a pharmaceutically acceptable salt or solvate thereof, R1 is C1-3 linear alkyl, C3 branched alkyl, or optionally substituted phenyl.

In one embodiment, in compound of formula I, II or III or a pharmaceutically acceptable salt or solvate thereof, R1 is C1-6 linear or C3-6 branched alkyl.

In one embodiment, in compound of formula I, II or III or a pharmaceutically acceptable salt or solvate thereof, R1 is C1-3 linear or C3 branched alkyl.

In one embodiment, in compound of formula I, II or III or a pharmaceutically acceptable salt or solvate thereof, R1 is an optionally substituted phenyl.

In one embodiment, in compound of formula I, II or III or a pharmaceutically acceptable salt or solvate thereof, R1 is methyl, ethyl, n-propyl, i-propyl, cyclopropyl or optionally substituted phenyl.

In one embodiment, in compound of formula I, II or III or a pharmaceutically acceptable salt or solvate thereof, R1 is methyl, ethyl, n-propyl, i-propyl or cyclopropyl.

In one embodiment, in compound of formula I, II or III or a pharmaceutically acceptable salt or solvate thereof, R6 is H, C1-6 linear alkyl or C3-6 branched alkyl, C3-6 cycloalkyl.

In one embodiment, in compound of formula I, II or III or a pharmaceutically acceptable salt or solvate thereof, R6 is H, C1-3 linear alkyl, C3 branched alkyl or C3 cycloalkyl.

In one embodiment, in compound of formula I, II or III or a pharmaceutically acceptable salt or solvate thereof, R6 is H.

In one embodiment, in compound of formula I, II or III or a pharmaceutically acceptable salt or solvate thereof, R6 is C1-3 linear alkyl.

In one embodiment, in compound of formula I, II or III or a pharmaceutically acceptable salt or solvate thereof, R6 is C3 branched alkyl.

In one embodiment, in compound of formula I, II or III or a pharmaceutically acceptable salt or solvate thereof, R6 is C3 cycloalkyl.

In one embodiment, in compound of formula I, II or III or a pharmaceutically acceptable salt or solvate thereof, R6 is H, methyl, ethyl, n-propyl, i-propyl or cyclopropyl.

In one embodiment, there is provided a compound of formula I, II or III or a pharmaceutically acceptable salt or solvate thereof, wherein X is CH, R1 is C1-6 linear or C3-6 branched alkyl, C3-6 cycloalkyl, or optionally substituted phenyl and R6 is H, C1-6 linear alkyl or C3-6 branched alkyl, C3-6 cycloalkyl. A first sub-selection of the previous embodiment is, when the compound (such as compound of formula I or II) comprises R2, R3, R4, R5, R7 and R8, that each of these variable are H.

In one embodiment, there is provided a compound of formula I, II or III or a pharmaceutically acceptable salt or solvate thereof, wherein X is CH, R1 is C1-3 linear alkyl, C3 branched alkyl, or optionally substituted phenyl and R6 is H, C1-3 linear alkyl, C3 branched alkyl or C3 cycloalkyl. A first sub-selection of the previous embodiment is, when the compound (such as compound of formula I or II) comprises R2, R3, R4, R5, R7 and R8, that each of these variable are H.

In one embodiment, there is provided a compound of formula I, II or III or a pharmaceutically acceptable salt or solvate thereof, wherein X is CH, R1 is C1-3 linear or C3 branched alkyl and R6 is H, C1-3 linear alkyl, C3 branched alkyl or C3 cycloalkyl. A first sub-selection of the previous embodiment is, when the compound (such as compound of formula I or II) comprises R2, R3, R4, R5, R7 and R8, that each of these variable are H.

In one embodiment, there is provided a compound of formula I, II or III or a pharmaceutically acceptable salt or solvate thereof, wherein X is CH, R1 is phenyl and R6 is H, C1-3 linear alkyl, C3 branched alkyl or C3 cycloalkyl. A first sub-selection of the previous embodiment is, when the compound (such as compound of formula I or II) comprises R2, R3, R4, R5, R7 and R8, that each of these variable are H.

In one embodiment, there is provided a compound of formula I, II or III or a pharmaceutically acceptable salt or solvate thereof, wherein X is CH, R1 is methyl, ethyl, n-propyl, i-propyl, cyclopropyl or optionally substituted phenyl and R6 is H, methyl, ethyl, n-propyl, i-propyl or cyclopropyl. A first sub-selection of the previous embodiment is, when the compound (such as compound of formula I or II) comprises R2, R3, R4, R5, R7 and R8, that each of these variable are H.

In one embodiment, there is provided a compound of formula I, II or III or a pharmaceutically acceptable salt or solvate thereof, wherein X is N, R1 is C1-6 linear or C3-6 branched alkyl, C3-6 cycloalkyl, or optionally substituted phenyl and R6 is H, C1-6 linear alkyl or C3-6 branched alkyl, C3-6 cycloalkyl. A first sub-selection of the previous embodiment is, when the compound (such as compound of formula I or II) comprises R2, R3, R4, R5, R7 and R8, that each of these variable are H.

In one embodiment, there is provided a compound of formula I, II or III or a pharmaceutically acceptable salt or solvate thereof, wherein X is N, R1 is C1-3 linear alkyl, C3 branched alkyl, or optionally substituted phenyl and R6 is H, C1-3 linear alkyl, C3 branched alkyl or C3 cycloalkyl. A first sub-selection of the previous embodiment is, when the compound (such as compound of formula I or II) comprises R2, R3, R4, R5, R7 and R8, that each of these variable are H.

In one embodiment, there is provided a compound of formula I, II or III or a pharmaceutically acceptable salt or solvate thereof, wherein X is N, R1 is R1 is C1-3 linear or C3 branched alkyl and R6 is H, C1-3 linear alkyl, C3 branched alkyl or C3 cycloalkyl. A first sub-selection of the previous embodiment is, when the compound (such as compound of formula I or II) comprises R2, R3, R4, R5, R7 and R8, that each of these variable are H.

In one embodiment, there is provided a compound of formula I, II or III or a pharmaceutically acceptable salt or solvate thereof, wherein X is N, R1 is phenyl and R6 is H, C1-3 linear alkyl, C3 branched alkyl or C3 cycloalkyl. A first sub-selection of the previous embodiment is, when the compound (such as compound of formula I or II) comprises R2, R3, R4, R5, R7 and R8, that each of these variable are H.

In one embodiment, there is provided a compound of formula I, II or III or a pharmaceutically acceptable salt or solvate thereof, wherein X is N, R1 is methyl, ethyl, n-propyl, i-propyl, cyclopropyl or optionally substituted phenyl I and R6 is H, methyl, ethyl, n-propyl, i-propyl or cyclopropyl. A first sub-selection of the previous embodiment is, when the compound (such as compound of formula I or II) comprises R2, R3, R4, R5, R7 and R8, that each of these variable are H.

In one embodiment, in compound of formula I and II, R2, R3, R4 and R5 are H or an independently selected substituent as defined herein.

In any one of the above embodiment, when the compound (such as compound of formula I or II) comprises R2, R3, R4, R5, R7 and R8, each of these variable can be H.

The term "alkyl" represents an optionally substituted linear or branched hydrocarbon moiety having 1 to 10 carbon atoms. Examples of "alkyl" groups include but are not limited to methyl, ethyl, propyl, isopropyl, butyl, isobutyl, sec-butyl, tert-butyl, pentyl, isopentyl, neopentyl, tert-pentyl, hexyl, isohexyl or neohexyl. Lower alkyls represent a linear or branched moiety having 1 to 6 or preferably 1 to 3 carbon atoms.

The term "cycloalkyl" represents optionally substituted cyclic hydrocarbon moiety having 3 to 10 carbon atoms. Examples of "cycloalkyl" groups include but are not limited to cyclopropyl, cyclobutyl, cyclopentyl, and cyclohexyl. Lower cycloalkyls comprise 3 to 6 or preferably 3 carbon atoms.

The terms "alkenyl" and "alkynyl" represent optionally substituted linear or branched hydrocarbon moiety which has one or more double bonds or triple bonds in the chain. The number of carbon atoms can be the same as those in "alkyl" provided that there is at least 2 carbon atoms. Examples of alkenyl, and alkynyl groups include but are not limited to, allyl, vinyl, acetylenyl, ethylenyl, propenyl, isopropenyl, butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl and hexynyl.

The terms "alkoxy," "alkenyloxy," and "alkynyloxy" represent an alkyl, alkenyl or alkynyl moiety, respectively, which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy.

As used herein, amino include amino which are unsubstituted such as —NH$_2$, or substituted with one or two C1-6alkyl or aryl such as —NH(C$_{1-6}$alkyl), —N(C$_{1-6}$alkyl)$_2$, —N(C$_{1-6}$alkyl)(aryl) and —N (aryl)$_2$.

The term "aryl" represents an optionally substituted carbocyclic moiety containing at least one benzenoid-type ring (i.e., may be monocyclic or polycyclic). Examples include but are not limited to phenyl, tolyl, dimethylphenyl, aminophenyl, anilinyl, naphthyl, anthryl, phenanthryl or biphenyl. Preferably, the aryl comprises 6 to 10 or more preferably 6 carbon atoms.

The term "aryloxy" represents an aryl moiety, which is covalently bonded to the adjacent atom through an oxygen atom. Examples include but are not limited to phenoxy, dimethylphenoxy, aminophenoxy, anilinoxy, naphthoxy, anthroxy, phenanthroxy or biphenoxy.

The term "arylalkyl" represents an aryl group attached to the adjacent atom by an alkyl, alkenyl or alkynyl. Examples include but are not limited to benzyl, benzhydryl, trityl, phenethyl, 3-phenylpropyl, 2-phenylpropyl, 4-phenylbutyl and naphthylmethyl.

The term "arylalkyloxy" represents an arylalkyl moiety, which is covalently bonded to the adjacent atom through an oxygen atom. Examples include but are not limited to benzyloxy, benzhydroxy, trityloxy, phenethyloxy, 3-phenylpropoxy, 2-phenylpropoxy, 4-phenylbutoxy and naphthylmethoxy.

The term "heterocycle" represents a 3 to 11 membered optionally substituted saturated, unsaturated, partially saturated or aromatic cyclic moiety wherein said cyclic moiety is interrupted by at least one heteroatom selected from oxygen (O), sulfur (S) or nitrogen (N). Heterocycles may be monocyclic or polycyclic rings.

Heterocycles may be 3 to 6 membered monocyclic ring or 5 to 6 membered monocyclic ring. Heterocycles may be 7 to 12 membered bicyclic ring or 9 to 10 membered bicyclic ring. Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl and thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

When heterocycle is a polycyclic ring, the rings comprise at least one ring comprising the heteroatom and the other rings may be cycloalkyl, aryl or heterocycle and the point of attachment may be on any available atom.

"Halogen atom" is specifically a fluorine atom, chlorine atom, bromine atom or iodine atom; preferably the halogen is a fluoride.

The term "optionally substituted", "optionally substituent" or "substituent" (such as for the definition of R2, R3, R4 and R5 herein above) represents at each occurrence and independently, one or more halogen, amino, amidino, amido, azido, cyano, guanido, hydroxyl, nitro, nitroso, urea, $OS(O)_2Rm$ (wherein Rm is selected from C1-6alkyl, C6-10aryl or 3-10 membered heterocycle), $OS(O)_2ORn$ (wherein Rn is selected from H, C1-6alkyl, C6-10aryl or 3-10 membered heterocycle), $S(O)_2ORp$ (wherein Rp is selected from H, C1-6alkyl, C6-10aryl and 3-10 membered heterocycle), $S(O)_{0-2}Rq$ (wherein Rq is selected from H, C1-6alkyl, C6-10aryl or 3-10 membered heterocycle), OP(O)ORsORt, P(O)ORsORt (wherein Rs and Rt are each independently selected from H or C1-6alkyl), C1-6alkyl, C6-10aryl-C1-6alkyl, C6-10aryl, C1-6alkoxy, C6-10aryl-C1-6alkyloxy, C6-10aryloxy, 3-10 membered heterocycle, C(O)Ru (wherein Ru is selected from H, C1-6alkyl, C6-10aryl, C6-10aryl-C1-6alkyl or 3-10 membered heterocycle), C(O)ORv (wherein Rv is selected from H, C1-6alkyl, C6-10aryl, C6-10aryl-C1-6alkyl or 3-10 membered heterocycle), NRxC(O)Rw (wherein Rx is H or C1-6alkyl and Rw is selected from H, C1-6alkyl, C6-10aryl, C6-10aryl-C1-6alkyl or 3-10 membered heterocycle, or Rx and Rw are taken together with the atoms to which they are attached to form a 3 to 10 membered heterocycle) or SO2NRyRz (wherein Ry and Rz are each independently selected from H, C1-6alkyl, C6-10aryl, C3-10heterocycle or C6-10aryl-C1-6alkyl).

In another embodiment, the term "optionally substituted", "optionally substituent" or "substituent" preferably represents halogen, C1-6alkyl, C2-6alkenyl, C2-6alkynyl, C1-6 alkoxy, C2-6alkenyloxy, C2-6alkynyloxy, —NR40R41, —C(O)NR40R41, —NR40COR41, carboxy, azido, cyano, hydroxyl, nitro, nitroso, —OR40, —SR40, —S(O)$_{0-2}$R40, —C(O)R40, —C(O)OR40 and —SO$_2$NR40R41; wherein R40 and R41 are each independently H, C1-6alkyl, C2-6alkenyl or C2-6alkynyl.

In still another embodiment, the term "optionally substituted", "optionally substituent" or "substituent" preferably represents halogen, C1-6alkyl, C2-6alkenyl, C1-6 alkoxy, —NR40R41, —C(O)NR40R41, —NR40COR41, carboxy, hydroxyl, nitro, —SR40, —S(O)$_{0-2}$R40, —C(O)R40, —C(O)OR40 and —SO$_2$NR40R41; wherein R40 and R41 are each independently H, or C1-6alkyl.

The term "independently" means that a substituent can be the same or a different definition for each item.

As defined herein "subject" refers to both human and non-human subjects. Preferably the subject is human.

The compounds as defined herein may include a chiral center which gives rise to enantiomers. The compounds may thus exist in the form of two different optical isomers, that is (+) or (−) enantiomers. All such enantiomers and mixtures thereof, including racemic or other ratio mixtures of individual enantiomers, are included within the scope of the invention. The single enantiomer can be obtained by methods well known to those of ordinary skill in the art, such as chiral HPLC, enzymatic resolution and chiral auxiliary derivatization.

It will also be appreciated that the compounds in accordance with the present disclosure can contain more than one chiral centre. The compounds of the present invention may thus exist in the form of different diastereomers. All such diastereomers and mixtures thereof are included within the scope of the invention. The single diastereomer can be obtained by methods well known in the art, such as HPLC, crystallisation and chromatography.

There is also provided pharmaceutically acceptable salts of the compounds of the present disclosure. What is meant by the term pharmaceutically acceptable salts of the compounds is that they are derived from pharmaceutically acceptable inorganic and organic acids and bases.

For example, conventional non-toxic salts include those derived from inorganic acids such as hydrochloric, hydrobromic, sulfuric, sulfamic, phosphoric, nitric, perchloric and the like, as well as salts prepared from organic acids such as formic, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, benzenesulphonic, naphthalene-2-sulphonic, ethane disulfonic, oxalic, isethionic, trifluoroacetic and the like.

Other acids, while not in themselves pharmaceutically acceptable, may be useful as intermediates in obtaining the compounds of the disclosure and their pharmaceutically acceptable acid addition salts. Salts derived from appropriate bases include alkali metal, alkaline earth metal or ammonium salts. The salt(s) must be "acceptable" in the sense of not being deleterious to the recipient thereof.

The pharmaceutically acceptable salts of the compounds of this disclosure can be synthesized from the compounds of this disclosure which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The term "Solvate" means that a compound as defined herein incorporates one or more pharmaceutically acceptable solvents including water to give rise to hydrates. The solvate may contain one or more molecules of solvent per molecule of compound or may contain one or more molecules of compound per molecule of solvent. Illustrative non-limiting examples of hydrates include monohydrate, dihydrate, trihydrate and tetrahydrate or semi-hydrate. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

It will be appreciated by those skilled in the art that the compounds in accordance with the present disclosure can exist in several different crystalline forms due to a different arrangement of molecules in the crystal lattice. This may include solvate or hydrate (also known as pseudopolymorphs) and amorphous forms. All such crystalline forms and polymorphs are included within the scope of the disclosure. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC) differential thermal analysis (DTA), thermogravimetric analysis (TGA)), Raman spectroscopy, comparative intrinsic dissolution rate, scanning electron microscopy (SEM).

When there is a sulfur atom present, the sulfur atom can be at different oxidation levels, ie. S, SO, or $SO_2$. All such oxidation levels are within the scope of the present disclosure.

When there is a nitrogen atom present, the nitrogen atom can be at different oxidation levels, ie. N or NO. All such oxidation levels are within the scope of the present disclosure.

In accordance with one embodiment, there is provided the uses, methods and compositions described herein wherein the compound is any compound as defined herein including any of compounds defined in formula I, II and III.

The compounds provided herein may be useful in the treatment of a condition associated with a lowered level of insulin secretion. As used herein, these conditions are commonly linked by the fact that the afflicted subject produces a lower plasma level of insulin than a healthy subject (e.g. normoglycemic), such that the afflicted subject become hyperglycemic. In these conditions, the pancreatic β-cells of the afflicted subject secrete less insulin that the pancreatic β-cells of the healthy subject.

Insulin resistance is a condition in which body cells become less sensitive to the glucose-lowering effects of insulin. Insulin resistance in muscle and fat cells reduces glucose uptake (and so local storage of glucose as glycogen and triglycerides, respectively), whereas insulin resistance in liver cells results in reduced glycogen synthesis and storage and a failure to suppress glucose production and release into the blood. Insulin resistance normally refers to reduced glucose-lowering effects of insulin. However, other functions of insulin can also be affected. For example, insulin resistance in fat cells reduces the normal effects of insulin on lipids and results in reduced uptake of circulating lipids and increased hydrolysis of stored triglycerides. Increased mobilization of stored lipids in these cells elevates free fatty acids in the blood plasma. Elevated blood fatty-acid concentrations, reduced muscle glucose uptake, and increased liver glucose production all contribute to elevated blood glucose levels. If insulin resistance exists, more insulin needs to be secreted by the pancreas. If this compensatory increase does not occur, blood glucose concentrations increase and type II diabetes occurs. As such, the compounds identified herein could be useful in the treatment of symptoms or prevention of insulin resistance.

One of the conditions associated with a lowered insulin level is diabetes. Diabetes can be divided into two broad type of diseases: type I and type II diabetes.

Another condition associated with a lowered level of insulin secretion is metabolic syndrome. Metabolic syndrome is generally used to define a constellation of abnormalities that is associated with increased risk for the development of type II diabetes and atherosclerotic vascular disease. Related conditions and symptoms include, but are not limited to, fasting hyperglycemia (diabetes mellitus type II or impaired fasting glucose, impaired glucose tolerance, or insulin resistance), high blood pressure; central obesity (also known as visceral, male-pattern or apple-shaped adiposity), overweight with fat deposits mainly around the waist; decreased HDL cholesterol; elevated triglycerides.

Associated diseases can also include hyperuricemia, fatty liver (especially in concurrent obesity) progressing to non-alcoholic fatty liver disease, polycystic ovarian syndrome (in women), and acanthosis nigricans.

In one embodiment, "deficient insulin secretion" means insufficient insulin secretion.

In one embodiment, the condition associated with an insufficient insulin secretion is at least one of the following condition: diabetes (such as type I and II diabetes) and metabolic syndrome.

In one embodiment, the compounds suitable for certain uses as described herein may be viewed as those either being able to upregulate monoacylglyceride (MAG) level or increases the value of the MAG level with respect a control value and/or as being able to inhibit ABHD6 polypeptide activity or expression in the pancreatic β-cells of a subject in need thereof. In an embodiment, MAG is 2-monoacylglycerol. In an embodiment, MAG is 1-monoacylglycerol. The "acyl" portion of said acylglycerol is not particularly limited and is a hydrocarbon chain from 2 to 26 carbons, straight or branched, saturated or unsaturated with one or more double bond, of either E or Z stereochemistry where applicable. In one embodiment, the compound are selectively inhibiting ABHD6 versus diacylglycerol lipase in at least one effective concentration. Preferably, the compound activity and/or selectivity will result in a increased insulin secretion in the subject.

In one embodiment, in a method or use as defined herein, the compound can be any compound as defined herein with the possible exception of any one of compounds i) to iv) as provided herein. The proviso can be any of i) to iv) or a combination of said compounds thereof. For example, the method or use of a compounds defined herein for inhibiting ABHD6 in a subject in need thereof, is comprising a therapeutically effective amount of a compound I, II or III or a pharmaceutically acceptable salt or solvate thereof, provided that it is other than compound i) and iv).

The excipient(s) for use in pharmaceutical compositions in accordance with the disclosure must be "pharmaceutically acceptable" in the sense of being compatible with the other ingredients of the formulation and not being deleterious to the recipient thereof.

In another embodiment, the present disclosure provides a combination comprising a therapeutically effective amount of a compound, as defined herein, and a therapeutically effective amount of at least one or more therapeutic agents useful in the method of the present disclosure.

It will be clear to a person of ordinary skill that if a further additional therapeutic agent is required or desired, ratios will be readily adjusted. It will be understood that the scope of combinations described herein is not particularly limited, but includes in principle any therapeutic agent useful for the prevention and treatment of diseases and conditions described herein such as diabetes and metabolic syndrome. Also included as additional therapeutic agents are insulin or insulin conjugate or derivative or agents, other than those of the present disclosure, that increase or stimulates insulin secretion.

It will be appreciated that the amount of a compound of the description required for use in treatment will vary not only with the particular compound selected but also with the route of administration, the nature of the condition for which treatment is required and the age and condition of the patient and will be ultimately at the discretion of the attendant physician.

The desired dose may conveniently be presented in a single dose or as divided dose administered at appropriate intervals, for example as two, three, four or more doses per day.

The compounds can, for example, be administered orally, mucosally (including sublingual, buccal, rectal, nasal or vaginal administrations), parenterally (including subcutaneous injection, bolus injection, intraarterial, intravenous, intramuscular, intrasternal injection or infusion administrations techniques), by inhalation spray, transdermal, such as passive or iontophoretic delivery, or topical administration, in the form of a unit dosage of a pharmaceutical composition containing an effective amount of the compound and conventional non-toxic pharmaceutically-acceptable carriers.

The formulations may, where appropriate, be conveniently presented in discrete dosage units and may be prepared by any of the methods well known in the art of pharmacy. The methods for preparing a pharmaceutical composition can include the steps of bringing into association the compound as defined herein and pharmaceutically acceptable carriers and then, if necessary, shaping the product into the desired formulation, including applying a coating when desired.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile water or saline, before use.

Compositions suitable for topical administration in the mouth include lozenges comprising the active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

For administration by inhalation, the compounds and combinations as defined herein may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

Further description of methods suitable for use in preparing pharmaceutical compositions for use in the present disclosure and of ingredients suitable for use in said compositions is provided in Remington's Pharmaceutical Sciences, 18(th) edition, edited by A. R. Gennaro, Mack Publishing Co., 1990.

Examples of compounds suitable for use in accordance with the present disclosure is provided in Table 1:

TABLE 1

| Compound # | Structure |
| --- | --- |
| 1 | 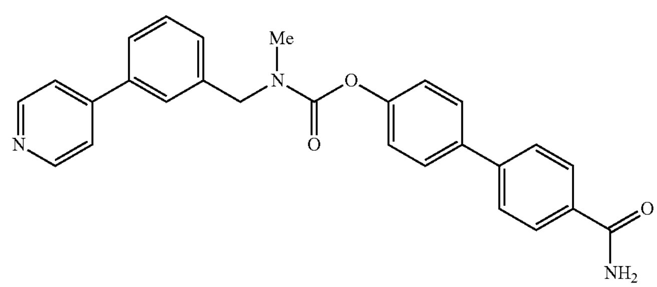 |
| 2 | 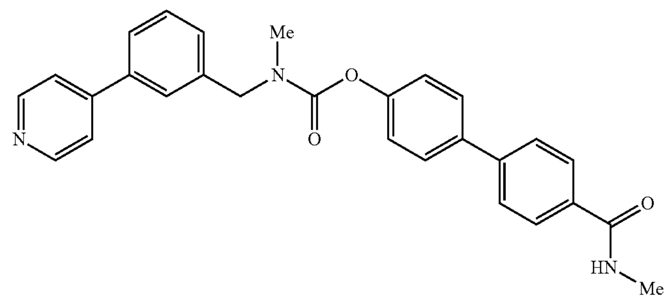 [SMILES: CNC(=O)c1ccc(-c2ccc(OC(=O)N(C)Cc3cccc(-c4ccncc4)c3)cc2)cc1] |

TABLE 1-continued

| Compound # | Structure |
|---|---|
| 3 | 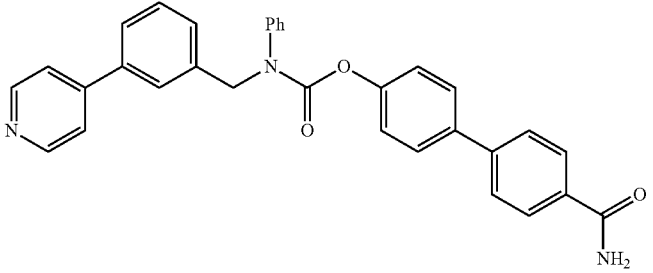 [SMILES: NC(=O)c1ccc(-c2ccc(OC(=O)N(Cc3cccc(-c4ccncc4)c3)c3ccccc3)cc2)cc1] |
| 4 | 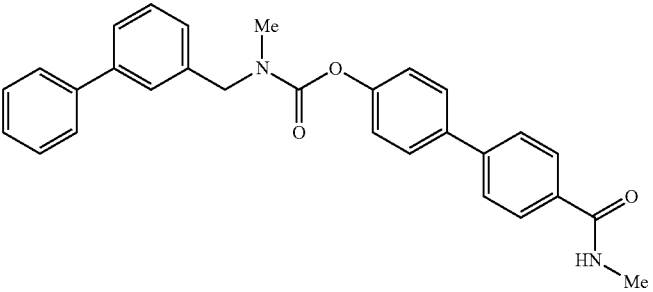 [SMILES: CNC(=O)c1ccc(-c2ccc(OC(=O)N(C)Cc3cccc(-c4ccccc4)c3)cc2)cc1] |
| 5 | 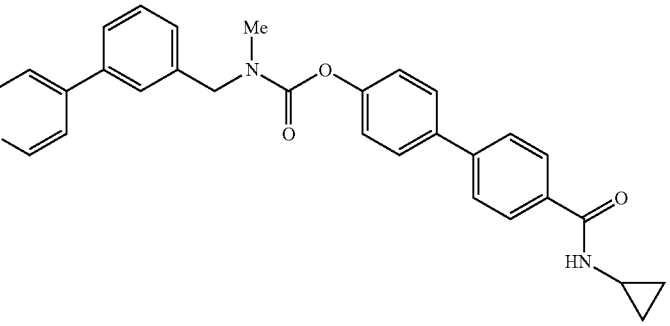 |
| 6 | 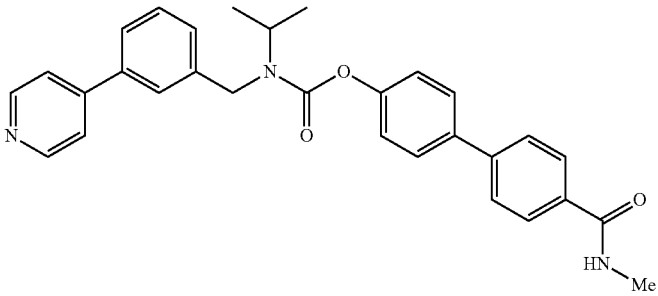 [SMILES: CNC(=O)c1ccc(-c2ccc(OC(=O)N(Cc3cccc(-c4ccncc4)c3)C(C)C)cc2)cc1] |

Preparation of the Compounds of the Disclosure

The compounds of the present disclosure can be prepared according to the procedures denoted in the following reaction Scheme. Examples or modifications thereof using readily available starting materials, reagents, and conventional procedures or variations thereof well-known to a practitioner of ordinary skill in the art of synthetic organic chemistry. Specific definitions of variables in the Schemes are given for illustrative purposes only and are not intended to limit the procedures described.

The starting materials and reagents used in preparing these compounds generally are either available from commercial sources or are prepared by synthetic chemistry in accordance with methods described for example in as R. C. LaRock, Comprehensive Organic Transformations, 2.sup.nd edition Wiley-VCH, New York 1999; and Organic Reactions, Wiley & Sons: New York, 1991, Volumes 1-40.

The compounds and or intermediates can be isolated and purified if necessary using known methods such as distillation, crystallization and chromatography.

The compounds of formula (1) and (2) depicted in scheme 1 below can be obtained from a commercial source or prepared in accordance with known synthetic chemistry methods. As illustrated in Scheme 1, a compound of formula (1) can be reacted with a proper "activating" reagent to form compound of formula (1-1) in which L is a leaving group suitable for the following step such as a halogen (e.g. chloride) or hydroxysuccinimide. R10 can be —(CO)NHR6' or a precursor thereof, wherein R6' is H, a protecting group or R6 as defined herein and R4 and R5 are as defined herein. Compound (1-1), with or without a prior step of isolation and purification, is reacted with a compound of formula (2) to provide a compound of formula (3). In compound of formula (2), X, R2, R3, R7 and R8 are as defined herein; R1' is H, a protecting group or R1 as defined herein. The compound of formula (3) can optionally be deprotected and/or modified as required on substituents R1' and R10 to provide the compound of formula (I) however when compound of formula (3) represents a compound in which R1' is R1 and R10 is —(CO)NHR6, then no further chemical modification may be required except for the optional preparation of a salt of compound (I). A similar process could be used based on the use of compounds (1) and (2-1).

Scheme 1 General synthesis

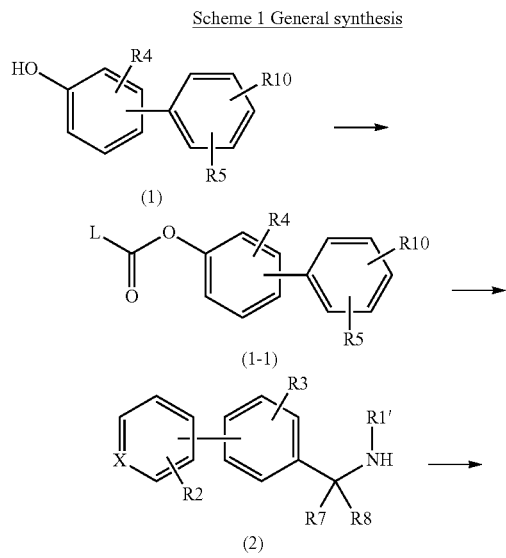

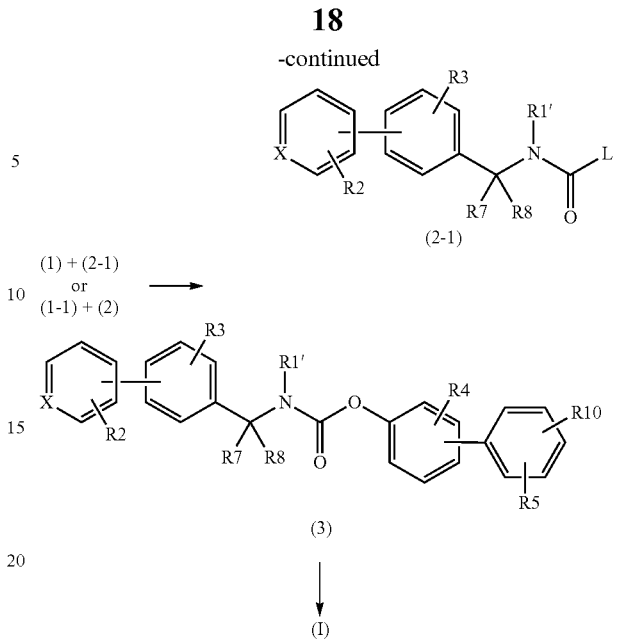

A particular selection of the compounds of the present disclosure is illustrated by formula (III) defined hereinbefore. The compounds of formula (1a) and (2a) depicted in scheme 2 below can be obtained from a commercial source or prepared in accordance with known synthetic chemistry methods. In this particular example, a compound of formula (1a) can be reacted with a reagent of formula (4) in a suitable solvent (such as $CH_3CN$) and in the presence of a base (such as $Et_3N$) to provide the intermediate compound (1-1a). Compound (1-1a) or suitable alternative such as carbamyl chloride, with or without a prior step of isolation and purification, is reacted with a compound of formula (2a) to provide a compound of formula (III). In scheme 2, X, R1 and R6 are as defined herein. A particular example of such substituents is when R1 is a phenyl, a methyl or isopropyl; when R6 is H, a methyl or a cyclopropyl and X is CH or N.

Scheme 2

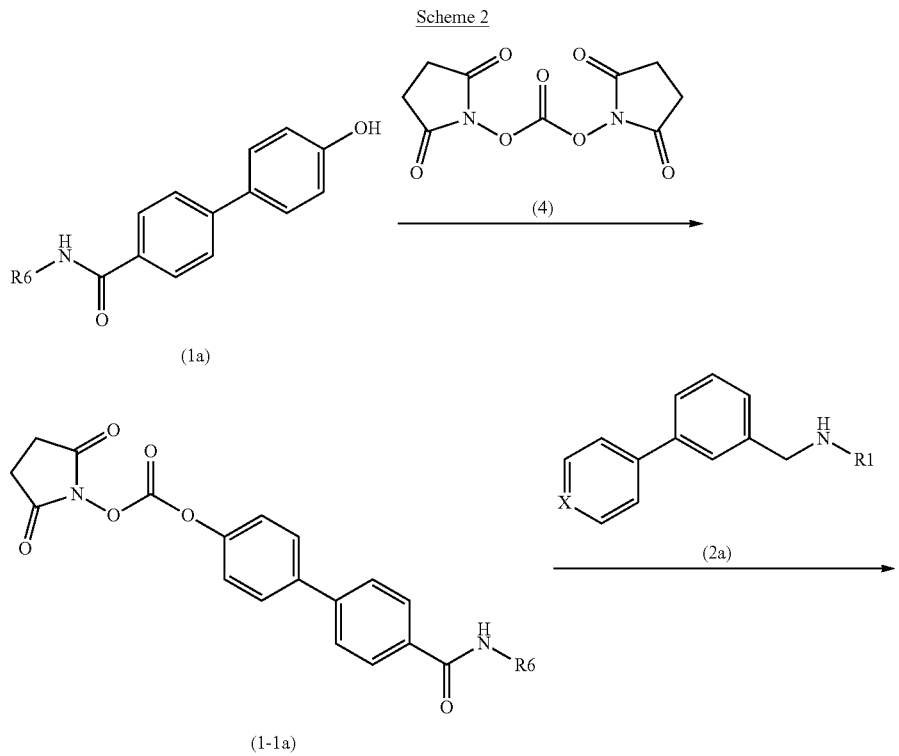

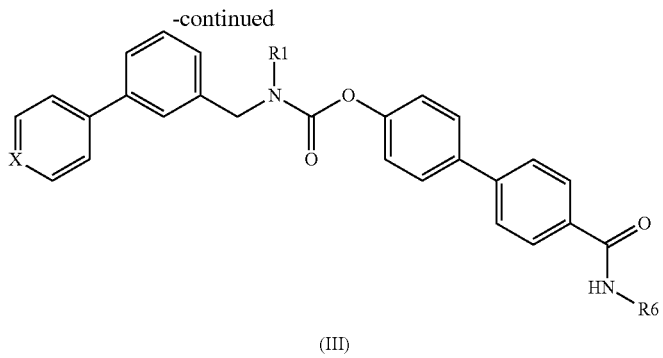

(III)

The following examples are provided to further illustrate details for the preparation and use of the compounds of the present disclosure. They are not intended to be limitations on the scope of the instant disclosure in any way, and they should not be so construed. Furthermore, the compounds described in the following examples are not to be construed as forming the only genus that is considered as the disclosure, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

Abbreviations Used in the Description of the Preparation of the Compounds of the Present Disclosure:

DSC=N,N'-Disuccinimidyl carbonate; HOBt=Hydroxybenzotriazole; EDCI=1-ethyl-3-(3-dimethylaminopropyl) carbodiimide; TLC=Thin layer chromatography; THF=Tetrahydofuran; DMF=N,N-Dimethylformamide; TFA=trifluoroacetic acid; RT=Room temperature; Ph=phenyl; Ac=acetyl; MeOH=Methanol; Et=Ethyl; AcOH=acetic acid; DMSO=Dimethyl sulfoxide.

WWL70 (corresponding to compound #1 in table 1 above) was obtained from Cayman Chemical Company. Orlistat was purchased from Sigma.

Example 1

4'-(Methylcarbamoyl)biphenyl-4-yl N-methyl-N-(3-(pyridin-4-yl)benzyl)carbamate (compound 2)

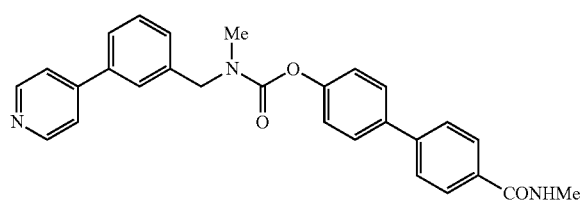

Step 1

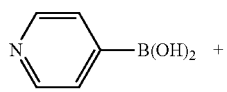

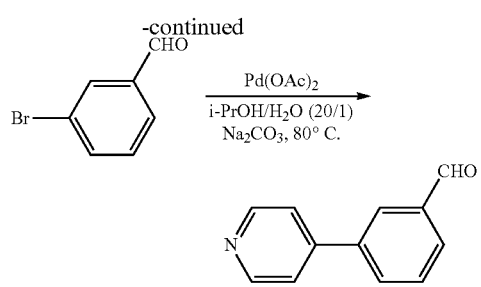

Into a 2 L 3-necked round-bottom flask, purged and maintained with an inert atmosphere of nitrogen, was placed a solution of pyridin-4-ylboronic acid (30 g, 244 mmol, 1 equiv) in 2-propanol/water (800/40 mL), Na$_2$CO$_3$ (77.3 g, 729 mmol, 3 equiv), Pd(OAc)$_2$ (5.46 g, 24.3 mmol, 0.1 equiv), PPh$_3$ (12.75 g, 48.7 mmol, 0.2 equiv) and 3-bromobenzaldehyde (45 g, 243 mmol, 1 equiv). The mixture was stirred for 48 h at 80° C. in an oil bath. Then the solids were filtered out and the filtrate was concentrated under vacuum. The residue was purified by column chromatography on silica gel (eluting with 1:1 ethyl acetate/petroleum ether) to give 30 g of 3-(pyridin-4-yl)benzaldehyde as orange oil.

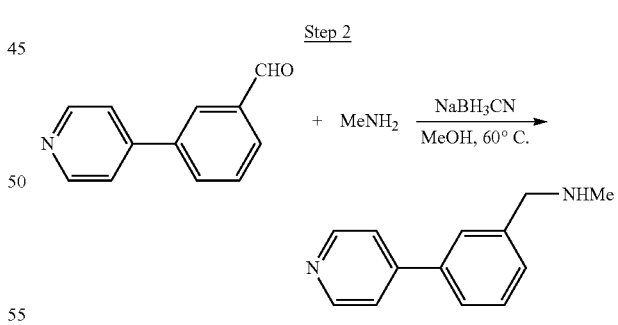

Into a 250 mL round-bottom flask was placed a solution of 3-(pyridin-4-yl)benzaldehyde (10 g, 54.6 mmol, 1 equiv) in MeOH (200 mL), NaBH$_3$CN (10.33 g, 164 mmol, 3 equiv) and CH$_3$NH$_2$.HCl (18.44 g, 273 mmol, 5 equiv). The mixture was stirred overnight at 60° C. The solvents were removed under reduced pressure. The residue was added to 100 mL of H$_2$O and extracted with 5×200 mL of ethyl acetate. After removal of solvent, the crude product was purified by re-crystallization from ethyl acetate to give 5 g of N-methyl-(3-(pyridin-4-yl)phenyl)methylamine as a white solid.

Step 3

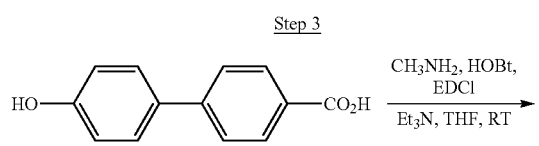

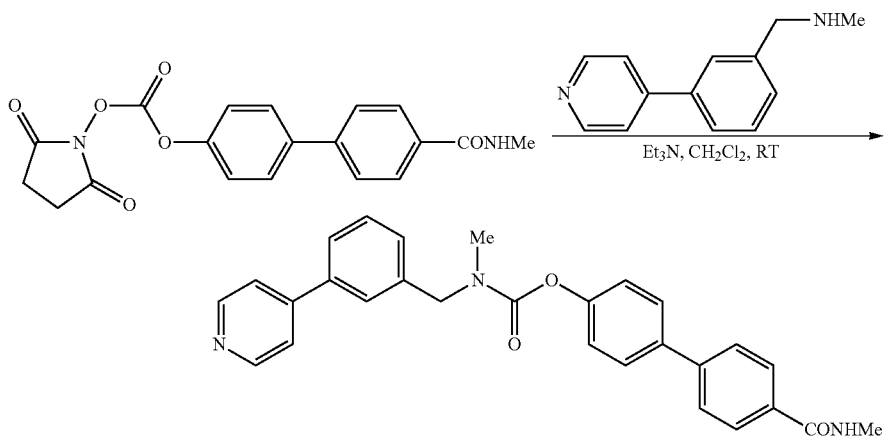

-continued

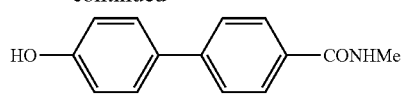

Into a 50-mL round-bottom flask was placed a solution of 4-(4-hydroxyphenyl)benzoic acid (1 g, 4.7 mmol, 1 equiv) in tetrahydrofuran (20 mL), methylamine hydrochloride, (0.409 g 6 mmol, 1.3 equiv), EDCI (1.18 g, 6.2 mmol, 1.3 equiv), HOBt (0.74 g, 5.5 mmol, 1.2 equiv), and triethylamine (2 mL). The resulting solution was stirred overnight at room temperature. The solids were filtered out. The resulting mixture was concentrated under vacuum. The residue was purified by column chromatography on silica gel (eluting with 15:2 ethyl acetate/petroleum ether) to give 4-(4-hydroxyphenyl)-N-methylbenzamide as a white solid.

Step 4

Into a 50 mL round-bottom flask was placed a solution of 4-(4-hydroxyphenyl)-N-methylbenzamide (682 mg, 3 mmol, 1 equiv) in CH₃CN (35 mL), Et₃N (610 mg, 6.04 mmol, 2 equiv) and DSC (4.65 g, 18.2 mmol, 6 equiv). The resulting solution was stirred for 10 minutes at room temperature and it was monitored by TLC. When the reaction was complete, the reaction mixture was diluted with 100 mL of ethyl acetate, washed with 3×30 mL of 5% citric acid. The organic layer was washed with 20 mL of brine, dried over anhydrous sodium sulfate, filtered and concentrated under vacuum. The resulting crude product was used as such in the next step.

Step 5

Into a 100 mL round-bottom flask was placed a solution of succinimidyl carbonate derivative from Step 4 (958 mg, 2.6 mmol, 1 equiv), Et₃N (260 mg, 2.57 mmol, 1 equiv) and N-methyl(3-(pyridin-4-yl)phenyl)methanamine from step 2 (510 mg, 2.58 mmol, 1 equiv) in dichloromethane (35 mL). The reaction mixture was stirred overnight at room temperature. The solid were filtered out. The filtrate was concentrated under vacuum. The crude product was purified by Prep-HPLC with the following conditions (1#-Pre-HPLC-006 (Waters)): Column, 1#-PrepC-015 (Atlantis T3 19*150 186003698 011639092113 01); mobile phase, WATER with 0.05% TFA and CH₃CN (10% up to 76% in 13 min); Detector, UV 254 nm. The title compound was obtained as a white solid.

¹H-NMR (400 MHz, CDCl₃, ppm) δ: 3.09 (3H, d), 3.15 (3H, s, rotamer 1), 3.50 (3H, s, rotamer 2), 4.69 (2H, s, rotamer 2), 4.80 (2H, s, rotamer 1), 6.22 (1H, d), 7.21-7.26 (2H, m), 7.56-7.70 (8H, m), 7.79-7.86 (4H, m), 8.75 (2H, d). MS (ES, m/z): [M+H]⁺ 452

Example 2

4'-Carbamoylbiphenyl-4-yl N-phenyl-N-(4-(pyridin-4-yl)benzyl)carbamate, trifluoroacetate salt (compound 3)

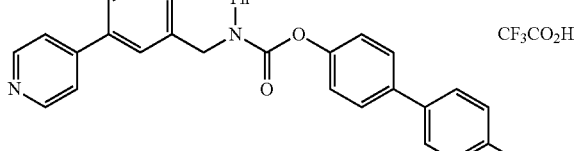

Step 1

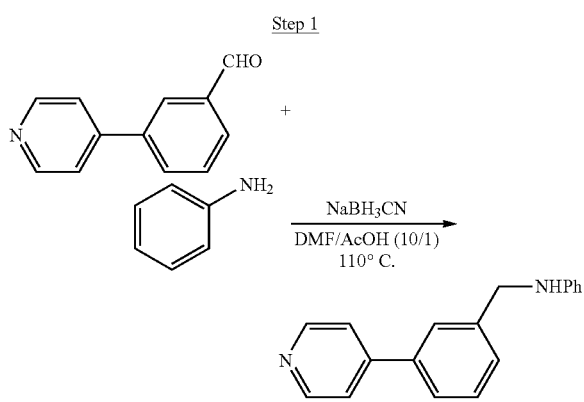

Into a 50-mL round-bottom flask, was placed a solution of 3-(pyridin-4-yl)benzaldehyde from Example 1 Step 1 (2 g, 10.9 mmol, 1 equiv) in DMF/AcOH (20/2 mL), aniline (1.02 g, 11.0 mmol, 1 equiv) and NaBH₃CN (2.62 g, 41.6 mmol, 4 equiv). The resulting solution was stirred 2 h at 110° C. The reaction was then quenched by the addition of 30 mL of water. The resulting solution was extracted with 30 mL of ethyl acetate, dried over anhydrous sodium sulfate, filtered and concentrated under vacuum. The residue was purified by column chromatography on silica gel (eluting with 1:1 ethyl acetate/petroleum ether) to give N-(3-(pyridin-4-yl)benzyl)benzenamine as light yellow oil.

Step 2

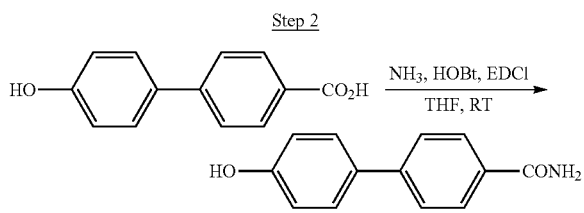

Into a 50-mL round-bottom flask was placed tetrahydrofuran saturated with NH₃ (gas) (20 mL), 4'-hydroxybiphenyl-4-carboxylic acid (1 g, 4.67 mmol, 1 equiv), HOBt (900 mg, 6.67 mmol, 1.4 equiv), EDCI (1.34 g, 7.0 mmol, 1.5 equiv). The resulting solution was stirred for 4 hrs at room temperature. The resulting mixture was concentrated under vacuum. The residue was dissolved in 50 mL of ethyl acetate, washed with 2×40 mL of H₂O, 1×50 mL of brine, dried over anhydrous sodium sulfate and concentrated under vacuum. The reside was purified by column chromatography on silica gel (eluting with 1:1 ethyl acetate/petroleum ether) to give 500 mg (50%) of 4'-hydroxybiphenyl-4-carboxamide as a white solid.

Step 3

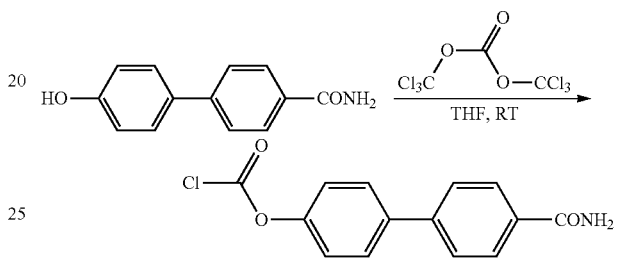

To a solution of triphosgene (1.8 g, 6.1 mmol, 2 equiv) in dichloromethane (15 mL) was added pyridine (2.5 mL) at −30° C. The reaction mixture was stirred for 15 min and a solution of 4'-hydroxylbiphenyl-4-carboxamide (658 mg, 3.08 mmol, 1 equiv) in dichloromethane (10 mL) was added. Then reaction mixture was warmed up to RT and stirred for 2 hours. The reaction was quenched by the addition of 10 mL of hydrogen chloride aqueous solution (1N). The resulting solution was extracted with 100 mL of dichloromethane. The organic phase was dried over anhydrous sodium sulfate, filtered and concentrated under vacuum. 4'-(carbamoyl)biphenyl-4-hydroxycarbamic chloride was obtained as a brown oil.

Step 4

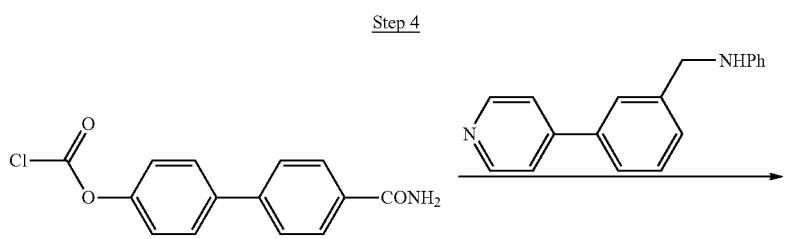

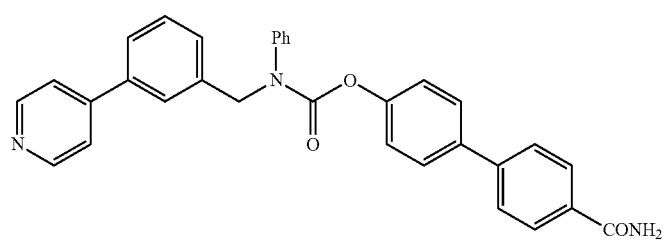

Into a 50 mL round-bottom flask, was placed a solution of the carbamic chloride from Step 3 (345 mg, 1.25 mmol, 1 equiv), N-(3-(pyridin-4-yl)benzyl)benzenamine from Step 1 (325 mg, 1.25 mmol, 1 equiv), potassium carbonate (344 mg, 2.49 mmol, 2.00 equiv) and DMF (15 mL). The reaction mixture was stirred for 3 hours at 110° C. The reaction was then quenched by the addition of 10 mL of water. The resulting solution was extracted with 2×25 mL of ethyl acetate. The organic layers were combined, washed with 2×10 mL of brine, dried over anhydrous sodium sulfate and concentrated under vacuum. The crude product (1.0 g) was purified by Prep-HPLC with the following conditions (1#-Pre-HPLC-016 (Waters)): Column, SunFire Prep C18, 19*150 mm 5 um; mobile phase, WATER with 0.05% TFA and CH$_3$CN (5% CH$_3$CN up to 36% in 27 min, up to 100% in 0.1 min, hold 100% in 1.9 min, down to 5% in 0.1 min, hold 5% in 1.9 min); Detector, UV 254 nm. The trifluoroacetate salt of the title compound was obtained as a white solid.

$^1$H-NMR (300 MHz, DMSO-d$_6$, ppm) δ: 5.15 (2H, s), 7.29-7.39 (3H, m), 7.42-7.50 (4H, m), 7.59-7.61 (2H, m), 7.75-7.78 (4H, m), 7.84-8.12 (7H, m), 8.87 (2H, d).

MS (ES, m/z): 500[M+H]$^+$

Example 3

4'-(Methylcarbamoyl)biphenyl-4-yl N-methyl-N-(3-phenylbenzyl)carbamate (compound 4)

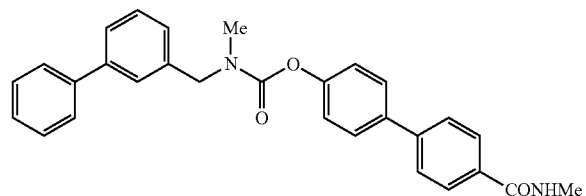

Step 1

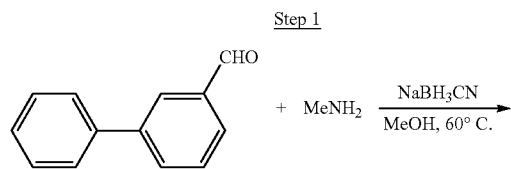

-continued

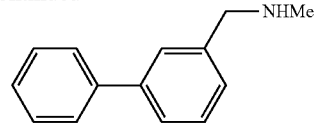

Into a 250-mL round-bottom flask was placed methanol (100 mL), acetic acid (42 mL), Biphenylcarboxaldehyde (7.96 g, 43.7 mmol, 1 equiv), methylamine in anhydrous ethanol (20 g, 193.2 mmol, 4.4 equiv), and NaBH$_3$CN (8.3 g, 132.1 mmol, 3 equiv). The solution was stirred overnight at 60° C. The resulting solution was diluted with 200 mL of water and extracted with 3×200 mL of ethyl acetate. The organic phase was dried over anhydrous sodium sulfate and concentrated under vacuum. The residue was applied onto a silica gel column with ethyl acetate/petroleum ether (1/10) to give N-methyl (3-biphenyl)methylamine as a colorless oil.

Step 2

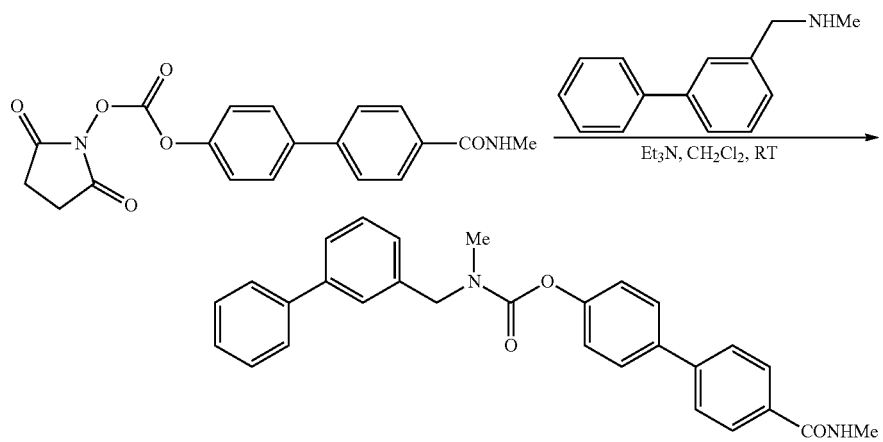

Into a 100-mL round-bottom flask was placed a solution of 4-[4-(methylcarbamoyl)phenyl]phenyl 2,5-dioxopyrrolidin-1-yl carbonate from Example 1 Step 4 (560 mg, 1.5 mmol, 1 equiv) in dichloromethane (40 mL), N-methyl (3-biphenyl)methylamine (301 mg, 1.5 mmol, 1 equiv) and triethylamine (153 mg, 1.5 mmol, 1 equiv). The resulting solution was stirred overnight at room temperature. The reaction mixture was washed with 2×20 mL of water and dried over anhydrous sodium sulfate. The resulting mixture was concentrated under vacuum. The crude product (650 mg) was purified by Prep-HPLC with the following conditions (1#-Pre-HPLC-002(Agilent)): Column, SunFire Prep C18, 19*150 mm 5 um; mobile phase, water and acetonitrile (10.0% acetonitrile up to 80.0% in 10 min, up to 100.0% in 1 min, down to 10.0% in 2 min); Detector, uv 220 & 254 nm. The title compound was obtained as a white solid.

$^1$H-NMR (400 MHz, DMSO-d$_6$, ppm) δ: 2.81 (3H, d), 2.98 (3H, s, rotamer 1), 3.08 (3H, s, rotamer 2), 4.60 (2H, s, rotamer 2), 4.74 (2H, s, rotamer 1), 7.22 (1H, d), 7.29 (1H, d), 7.33-7.41 (2H, m), 7.47-7.55 (3H, m), 7.61 (2H, broad s), 7.67 (2H, d), 7.76 (4H, broad d), 7.92 (2H, d), 8.49 (1H, d).

MS (ES, m/z): [M+H]$^+$ 451

Example 4

4'-(Cyclopropylcarbamoyl)biphenyl-4-yl N-methyl-N-(3-(pyridin-4-yl)benzyl)carbamate (compound 5)

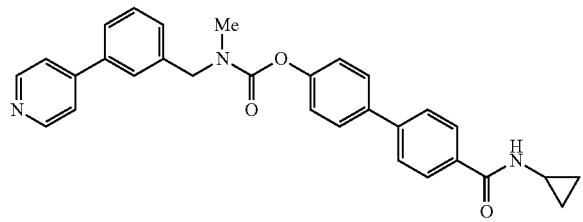 [SMILES: CN(Cc1cccc(-c2ccncc2)c1)C(=O)Oc1ccc(-c2ccc(C(=O)NC3CC3)cc2)cc1]

Step 1

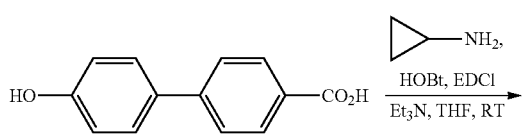

Step 2

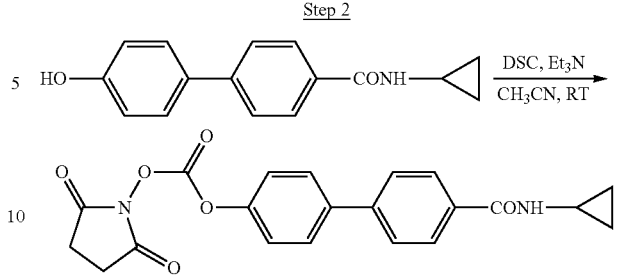

Into a 100-mL round-bottom flask was placed a solution of N-cyclopropyl 4-(4-hydroxyphenyl)benzamide (500 mg, 1.97 mmol, 1 equiv) in CH₃CN (60 mL), DSC (3 g, 11.71 mmol, 5.9 equiv), and triethylamine (400 mg, 3.95 mmol, 2 equiv). The resulting solution was stirred for 10 min at room temperature and was then diluted with 200 mL of ethyl acetate. The organic phase was washed with 2×100 mL of citric acid (5%), 1×50 mL of water, dried over anhydrous sodium sulfate and concentrated under vacuum. This resulted in 0.6 g (crude) of 4-[4-(cyclopropylcarbamoyl)phenyl]phenyl 2,5-dioxopyrrolidin-1-yl carbonate as a white solid.

Step 3

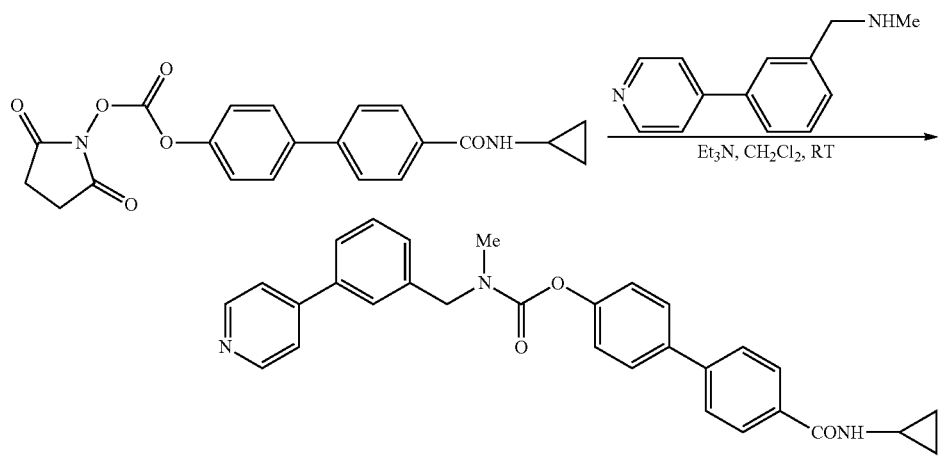

-continued

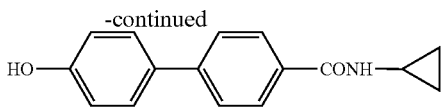

Into a 25-mL round-bottom flask was placed tetrahydrofuran (10 mL), cyclopropylamine (0.45 mL, 6.5 mmol, 1.4 equiv), 4-(4-Hydroxyphenyl)benzoic acid (1 g, 4.67 mmol, 1 equiv), HOBt (900 mg, 6.66 mmol, 1.43 equiv), EDCI.HCl (1.34 g, 6.99 mmol, 1.5 equiv) and the solution was stirred overnight at room temperature. The reaction mixture was diluted with 30 mL of brine and extracted with 4×30 mL of ethyl acetate. The organic phase was dried over anhydrous sodium sulfate and concentrated under vacuum. This resulted in N-cyclopropyl 4-(4-hydroxyphenyl)benzamide as a white solid.

Into a 100-mL round-bottom flask was placed a solution of 4-[4-(cyclopropylcarbamoyl)phenyl]phenyl 2,5-dioxopyrrolidin-1-yl carbonate (600 mg, 1.52 mmol, 1.00 equiv) in dichloromethane (40 mL), N-methyl ([[3-(pyridin-4-yl)phenyl]methyl])amine (301 mg, 1.52 mmol, 1.00 equiv) and triethylamine (153 mg, 1.51 mmol, 0.99 equiv). The resulting solution was stirred overnight at room temperature. The reaction mixture was washed with 2×20 mL of water and dried over anhydrous sodium sulfate. The resulting mixture was concentrated under vacuum. The crude product (650 mg) was purified by Prep-HPLC with the following conditions (1#-Pre-HPLC-002(Agilent)): Column, SunFire Prep C18, 19*150 mm 5 um; mobile phase, water and acetonitrile (10.0% acetonitrile up to 80.0% in 10 min, up to 100.0% in 1 min, down to 10.0% in 2 min); Detector, uv 220 & 254 nm. The title compound was obtained as a white solid.

¹H-NMR (400 MHz, DMSO-d₆, ppm) δ: 0.59 (2H, broad s), 0.71 (2H, broad s), 2.87 (1H, broad s), 2.98 (3H, s, rotamer 1), 3.09 (3H, s, rotamer 2), 4.62 (2H, s, rotamer 2), 4.76 (2H, s, rotamer 1), 7.22 (2H, dd), 7.46 (1H, m), 7.57 (1H, broad s), 7.75 (8H, broad m), 7.92 (2H, broad d), 8.48 (1H, s), 8.66 (2H, s).

MS (ES, m/z): [M+H]⁺ 478, [M+Na]⁺ 500

Example 5

4'-(Methylcarbamoyl)biphenyl-4-yl N-i-propyl-N-(3-(pyridin-4-yl)benzyl)carbamate (compound 6)

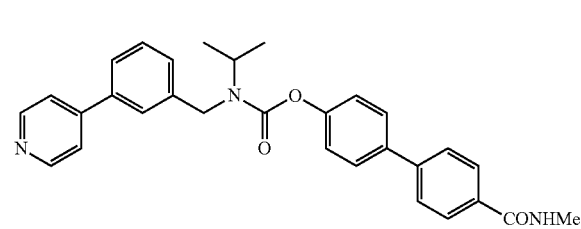

Step 1

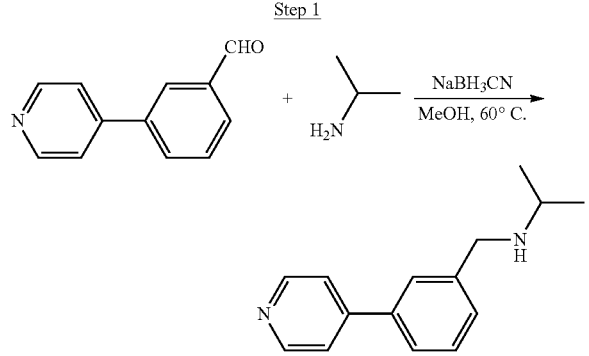

Into a 250-mL round-bottom flask was placed methanol (100 mL), acetic acid (42 mL), 3-(pyridin-4-yl)benzaldehyde from Example 1 Step 1 (8 g, 43.7 mmol, 1 equiv), isopropylamine (16.5 mL, 192 mmol, 4.4 equiv), and NaBH₃CN (8.3 g, 132 mmol, 3 equiv). The solution was stirred overnight at 60° C. The resulting solution was diluted with 200 mL of water and extracted with 3×200 mL of ethyl acetate. The organic phase was dried over anhydrous sodium sulfate and concentrated under vacuum. The residue was applied onto a silica gel column with ethyl acetate/petroleum ether (1/10). N-isopropyl (3-(pyridin-4-yl)phenylmethyl]) amine was obtained as a white solid.

Step 2

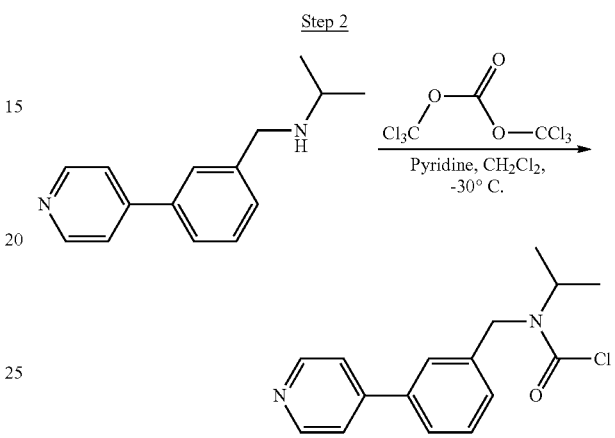

Into a 50-mL 3-necked round-bottom flask, purged and maintained with an inert atmosphere of nitrogen, was placed a solution of triphosgene (660 mg, 2.22 mmol, 2 equiv) in dichloromethane (10 mL). This was followed by the addition of pyridine (1.5 mL) at −30° C. The mixture was stirred 15 min. To this was added a solution of N-isopropyl 3-(4-pyridinyl)phenylmethylamine (256 mg, 1.13 mmol, 1 equiv) in dichloromethane (5 mL) at −30° C. The resulting solution was stirred for 90 min at −30° C. The reaction was then quenched by the addition of 5 mL of hydrochloric acid (1 N). The resulting solution was extracted with 20 mL of dichloromethane. The combined organic layers were dried over anhydrous sodium sulfate and concentrated under vacuum. This resulted in crude N-[3-(4-pyridinyl)phenylmethyl]-N-isopropylcarbamoyl chloride as light yellow oil.

Step 3

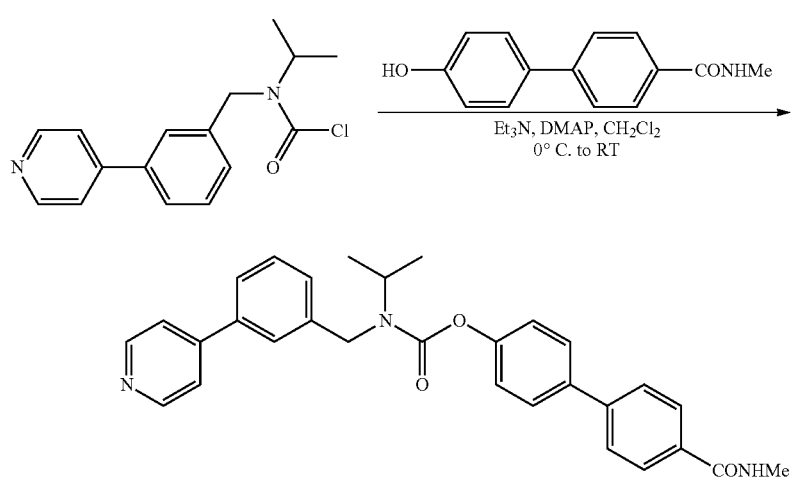

Into a 50-mL round-bottom flask was placed a solution of N-[3-(4-pyridinyl)phenylmethyl] N-isopropylcarbamoyl chloride (310 mg, 1.07 mmol, 1 equiv) in dichloromethane (15 mL), 4-(4-hydroxyphenyl)-N-methylbenzamide from Example 1 Step 3 (291 mg, 1.28 mmol, 1.2 equiv) and triethylamine (216 mg, 2.13 mmol, 2 equiv). The resulting solution was stirred overnight at room temperature. The reaction was then quenched by the addition of 10 mL of water. The resulting solution was extracted with 20 mL of dichloromethane. The organic layer was dried over anhydrous sodium sulfate and concentrated under vacuum. The crude product was purified by Prep-HPLC with the following conditions (1#-Pre-HPLC-002(Agilent)): Column, Xbridge Prep C18, 5 um, 19*150 mm; mobile phase, water and $CH_3CN$ (45.0% $CH_3CN$ up to 75.0% in 10 min, hold 100.0% in 1 min, hold 45.0% in 2 min); Detector, uv 220 & 254 nm. The title compound was obtained as a white solid.

$^1$H-NMR (400 MHz, DMSO-$d_6$, ppm) δ: 1.21 (6H, broad s), 2.80 (3H, d), 3.33 (3H, d), 4.36 (1H, broad m), 4.65 (2H, broad d), 7.15 (1H, d), 7.31 (1H, broad s), 7.45-7.65 (2H, m), 7.65-7.85 (8H, m), 7.91 (2H, d), 8.49 (1H, broad s), 8.65 (2H, d).

MS (ES, m/z): $[M+H]^+$ 480, $[M+Na]^+$ 502

Example 6

Inhibition of ABHD6 and DAGL

INS 832/13 β-cell extracts (whole cell) were prepared by sonication in Krebs-Ringer Buffer, pH7.4. Both ABHD6 and DAGL enzymes were assayed in a single incubation, with separate substrates. Cell extract, 10 μg was incubated in a final volume of 50 μl with 50 μM 1,2-dioleoylglycerol (substrate for DAGL) and 50 μM 1-palmitoylglycerol (substrate for ABHD6). Incubations were for 60 min at 30° C. and then the released fatty acids (oleate or palmitate) due to hydrolysis were extracted (Dole's extraction) and separated by HPLC (Mehta et al. Journal of Chromatography B, 719 (1998) pp 9-23) after derivatization by phenacylbromide. Quantification of oleate and palmitate released gave the activities of DAGL and ABHD6, respectively. Incubations contained indicated compounds at 10 μM (or as shown) concentration. WWL70 was used as a positive control for ABHD6 inhibition and orlistat (ORL) was used as a control for total lipase inhibition. Under the incubation conditions used, less than 1-2% of the added substrate was used up by either of the enzymes. The results are summarized in Table 2 below:

Example 7

Insulin Secretion

Materials.

Cell culture supplies were from Corning (Corning, N.Y.) and Fisherbrand (Canada). WWL70 was dissolved in dimethylsulfoxide (DMSO) before their use in insulin secretion experiments. Palmitate sodium salt was from Nu-Check Prep (Elysian, Minn.) and bicinchoninic acid protein assay kit from Pierce (Rockford, Ill.) was used. Stock unlabelled palmitate was prepared at 4 mM in 5% defatted BSA as described elsewhere (Roduit et al. Diabetes (2004) 53 pp 1007-1019,).

Cell culture. INS832/13 cells (Hohmeir et al. Diabetes (2000) 49 pp 424-430,) were cultured at 37° C. in a humidified atmosphere containing 5% $CO_2$ in RPMI 1640 with sodium bicarbonate, supplemented with 10% (v/v) fetal calf serum (Wisent), 10 mM HEPES, pH 7.4, 2 mM L-glutamine, 1 mM sodium pyruvate and 50 μM β-mercaptoethanol (complete RPMI). Cells were grown to 80% confluence. Media were changed to RPMI 1640 containing 3 mM glucose supplemented as the complete RPMI 24 h prior to the experiments. Insulin secretion incubations were conducted in Krebs-Ringer bicarbonate buffer containing 10 mM HEPES, pH 7.4 (KRBH).

Insulin secretion measurement. INS832/13 cells were washed in KRBH containing 1 mM glucose and 0.5% defatted BSA (KRBH 1 G/0.5% BSA) and pre-incubated for 45 min in KRBH 1 G/0.5% BSA in presence of pharmacological agents (at indicated concentrations) or vehicle (DMSO). For examining the effect of WWL70 (an inhibitor of ABHD6), other compounds identified in table 1, and/or orlistat (lipase inhibitor), the compounds were added first in pre-incubation media and then during incubation at 1 to 20 μM concentration (see Table-2) at 2 mM and 10 mM glucose. Insulin secretion from INS832/13 cells was measured from 2-h static incubations in KRBH containing various glucose concentrations, 0.5% defatted BSA and pharmacological agents or vehicle (DMSO), with or without 35 mM KCl or 0.3 mM palmitate, as specified (see Peyot et al., 2009—Adipose Triglyceride Lipase Is Implicated in Fuel- and Non-fuel-stimulated Insulin Secretion—*J Biol Chem*, 284: pp. 16848-16859). The experiments were done 3 times, with triplicates of each measurement.

TABLE 2

| Compound | Conc (μM) | Insulin secretion (% content) | ABHD6 Inhibition % | DAGL Inhibition % |
|---|---|---|---|---|
| Control | 0 | 1.95 | 0 | 0 |
| 1 | 2 | 3.22 | nd | nd |
|  | 5 | 3.97 | nd | nd |
|  | 10 | 6.03 | 95 | 0 |
| 2 | 2 | 2.25 | nd | nd |
|  | 5 | 3.70 | nd | nd |
|  | 10 | 6.08 | 98 | 0 |
| 3 | 2 | 2.00 | nd | nd |
|  | 5 | 2.10 | nd | nd |
|  | 10 | 3.05 | 90 | 0 |
| 4 | 2 | 3.05 | nd | nd |
|  | 5 | 3.65 | nd | nd |
|  | 10 | 3.82 | 70 | 0 |
| 5 | 2 | 2.01 | nd | nd |
|  | 5 | 2.05 | nd | nd |
|  | 10 | 3.56 | 60 | 10 |
| 6 | 2 | 3.10 | nd | nd |
|  | 5 | 3.98 | nd | nd |
|  | 10 | 5.88 | 95 | 0 | nd = not determined

Example 8

In Vivo Experiment

In this experiment—CD1 strain mice were injected once with streptozotocin (100 mg/kg body wt) to induce mild diabetes. After 4 weeks, the mice were fasted overnight and oral glucose tolerance test (OGTT) was done. Half the animals (5) received ABHD6 inhibitor, WWL70 for the three days prior to OGTT, daily, intraperitoneally (at 5 mg/kg body weight) and the other half received only vehicle. For OGTT, glucose was given by gavage (2 g/kg body wt), followed by blood collection at indicated time points (on the graph) for the analysis of blood glucose (by glucometer) and plasma insulin (by ELISA).

Figure 2:
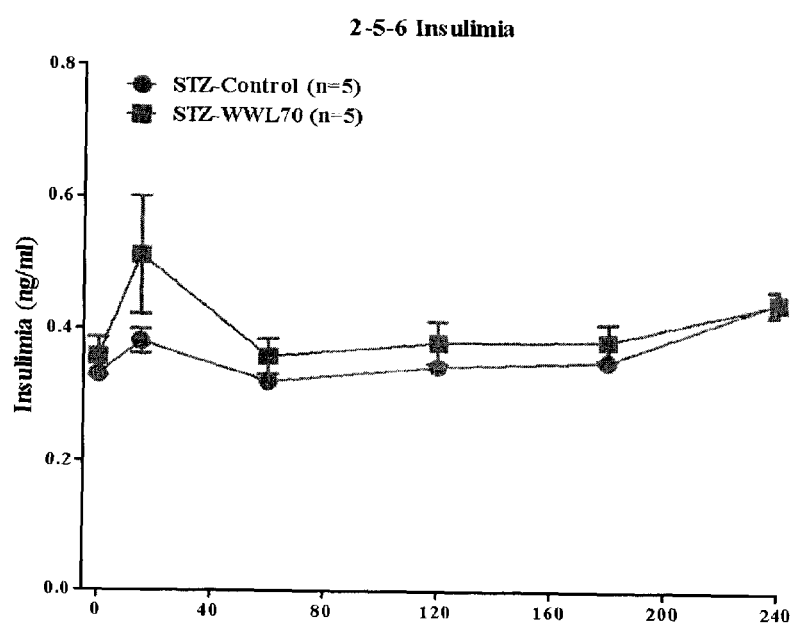

The results (see FIGS. 1 and 2) show that mice that received compound 1 (WWL70) were able to control their blood glucose levels better than the mice which were given vehicle. This is related to the increase in plasma insulin levels in mice that received compound 1—indicating that the compound increases insulin secretion in the presence of glucose and thus able to control glycemia.

While the disclosure has been described in connection with specific embodiments thereof, it is understood that it is capable of further modifications and that this application is intended to cover any variation, use, or adaptation of the disclosure following, in general, the principles of the disclosure and including such departures from the present disclosure that come within known, or customary practice within the art to which the disclosure pertains and as may be applied to the essential features hereinbefore set forth, and as follows in the scope of the appended claims.

The invention claimed is:

1. A compound of formula I

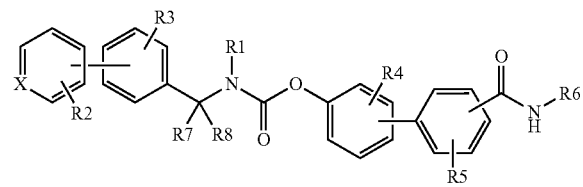

or a pharmaceutically acceptable salt or solvate thereof, wherein
X is N or CH;
R1 is lower linear or branched alkyl, cycloalkyl, lower linear or branched alkenyl, cycloalkenyl or aryl;
each of R2, R3, R4 and R5 is H or one or more independently selected substituent;
R6 is H, lower linear or branched alkyl, or cycloalkyl;
each of R7 and R8 is independently selected from H, lower alkyl or fluoride;
provided that said compound is other than compounds i), ii) iii) and iv)):

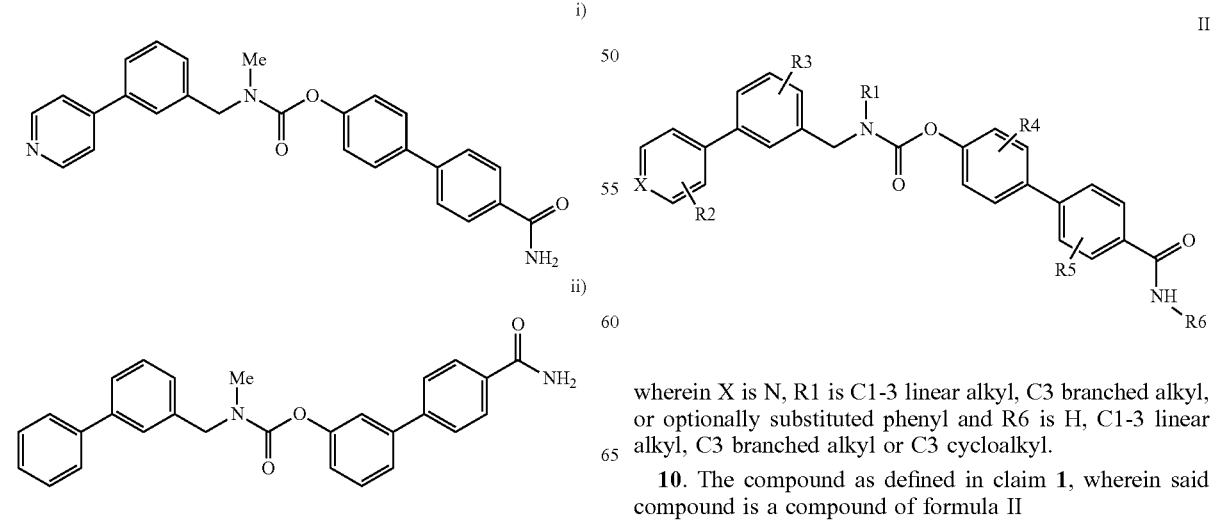

2. The compound of claim 1, wherein R1 is C1-6 linear or C3-6 branched alkyl, C3-6 cycloalkyl, or optionally substituted phenyl.

3. The compound of claim 1, wherein R6 is H, C1-6 linear alkyl or C3-6 branched alkyl, C3-6 cycloalkyl.

4. The compound of claim 1, wherein R2, R3, R4 and R5 are H or an independently selected substituent.

5. The compound of claim 1, wherein each of R7 and R8 is independently selected from H or C1-3 alkyl.

6. The compound of claim 1, wherein R2, R3, R4, R5, R7 and R8, are each H.

7. The compound as defined in claim 1, wherein said compound is a compound wherein X is CH, R1 is C1-3 linear alkyl, C3 branched alkyl, or optionally substituted phenyl and R6 is H, C1-3 linear alkyl, C3 branched alkyl or C3 cycloalkyl.

8. The compound as defined in claim 1, wherein said compound is a compound wherein X is N, R1 is C1-3 linear alkyl, C3 branched alkyl, or optionally substituted phenyl and R6 is H, C1-3 linear alkyl, C3 branched alkyl or C3 cycloalkyl.

9. The compound as defined in claim 1, wherein said compound is a compound of formula II wherein X is N, R1 is C1-3 linear alkyl, C3 branched alkyl, or optionally substituted phenyl and R6 is H, C1-3 linear alkyl, C3 branched alkyl or C3 cycloalkyl.

10. The compound as defined in claim 1, wherein said compound is a compound of formula II

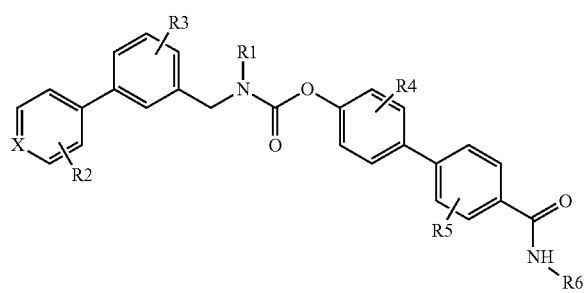
II
wherein X is CH, R1 is C1-3 linear alkyl, C3 branched alkyl, or optionally substituted phenyl and R6 is H, C1-3 linear alkyl, C3 branched alkyl or C3 cycloalkyl.
11. The compound of claim 9, wherein R2, R3, R4 and R5 are H.
12. The compound of claim 10, wherein R2, R3, R4 and R5 are H.
13. The compound of claim 1, wherein the compound is
| Compound # | Structure |
|---|---|
| 1 | 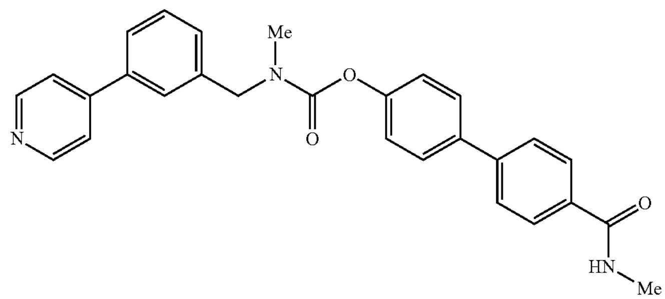 [SMILES: CNC(=O)c1ccc(-c2ccc(OC(=O)N(C)Cc3cccc(-c4ccncc4)c3)cc2)cc1] |
| 3 | 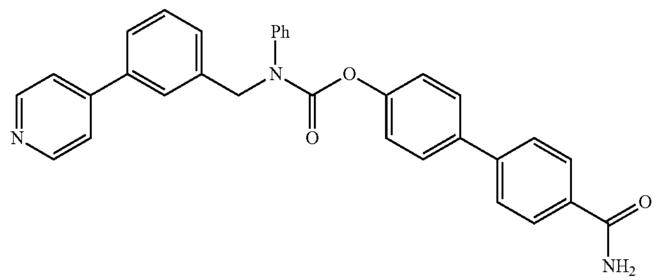 [SMILES: NC(=O)c1ccc(-c2ccc(OC(=O)N(Cc3cccc(-c4ccncc4)c3)c3ccccc3)cc2)cc1] |
| 4 | 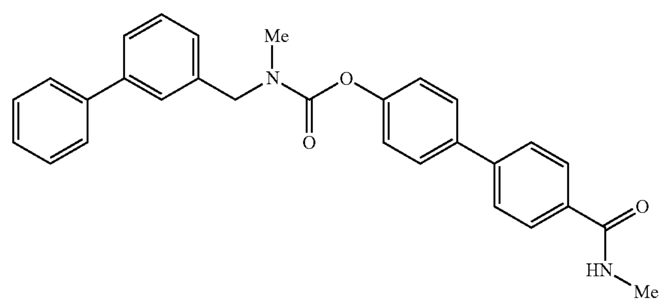 [SMILES: CNC(=O)c1ccc(-c2ccc(OC(=O)N(C)Cc3cccc(-c4ccccc4)c3)cc2)cc1] |
| 5 | or |

| Compound # | Structure |
|---|---|
| 6 | ![structure of compound 6: 4'-(methylcarbamoyl)biphenyl-4-yl (3-(pyridin-4-yl)benzyl)(isopropyl)carbamate] | or a pharmaceutically acceptable salt or solvate thereof.

14. A pharmaceutical composition comprising a compound as defined in claim 1, or a pharmaceutically acceptable salt or solvate thereof, and an acceptable excipient.

* * * * *